(12) United States Patent
Manwill et al.

(10) Patent No.: US 11,583,413 B2
(45) Date of Patent: Feb. 21, 2023

(54) EXPANDING INTERBODY SPACERS

(71) Applicant: Nexus Spine, L.L.C., Salt Lake City, UT (US)

(72) Inventors: Daniel Manwill, Riverton, UT (US); Peter Halverson, Draper, UT (US); David Hawkes, Pleasant Grove, UT (US)

( * ) Notice: Subject to any disclaimer, the term of this patent is extended or adjusted under 35 U.S.C. 154(b) by 0 days.

(21) Appl. No.: 16/297,585

(22) Filed: Mar. 8, 2019

(65) Prior Publication Data

US 2019/0274838 A1    Sep. 12, 2019

Related U.S. Application Data

(60) Provisional application No. 62/751,432, filed on Oct. 26, 2018, provisional application No. 62/736,924, filed on Sep. 26, 2018, provisional application No. 62/640,555, filed on Mar. 8, 2018.

(51) Int. Cl.
| | |
|---|---|
| *A61F 2/44* | (2006.01) |
| *A61F 2/46* | (2006.01) |
| *A61F 2/30* | (2006.01) |

(52) U.S. Cl.
CPC .......... *A61F 2/447* (2013.01); *A61F 2/4611* (2013.01); *A61F 2002/3007* (2013.01); *A61F 2002/3093* (2013.01); *A61F 2002/30476* (2013.01); *A61F 2002/30556* (2013.01); *A61F 2002/30579* (2013.01); *A61F 2002/30622* (2013.01); *A61F 2002/30784* (2013.01); *A61F 2002/4615* (2013.01)

(58) Field of Classification Search
CPC ....... A61F 2/447; A61F 2/4455; A61F 2/4611
See application file for complete search history.

(56) References Cited

U.S. PATENT DOCUMENTS

| | | | |
|---|---|---|---|
| 2010/0286783 A1* | 11/2010 | Lechmann | A61F 2/4455 623/17.12 |
| 2012/0116518 A1 | 5/2012 | Grotz et al. | |
| 2013/0123924 A1 | 5/2013 | Butler et al. | |

(Continued)

OTHER PUBLICATIONS

KIPO—International Search Report/Written Opinion from related case PCT/US2019/021499.

*Primary Examiner* — Ellen C Hammond
(74) *Attorney, Agent, or Firm* — Kirton McConkie; Adam D. Stevens

(57) ABSTRACT

An expandable interbody spacer includes a first endplate surface located on a first side of the spacer and adapted to contact a vertebral endplate surface of a first vertebral body, a second endplate surface located on a second, opposed, side of the spacer and adapted to contact a vertebral endplate surface of a second, opposed, vertebral body and an expansion mechanism adapted to selectively apply a distracting force between the first endplate surface and the second endplate surface, whereby actuation of the expansion mechanism causes the spacer to transition between a compressed insertion configuration to an expanded fusion configuration. The spacer also includes one or more of a deformable surface, a porosity to promote bone on-growth or through-growth, a stiffness substantially equivalent to cortical bone, and structure distributing loads through the spacer substantially without transferring the loads through higher-stiffness structures.

19 Claims, 38 Drawing Sheets

(56) References Cited

U.S. PATENT DOCUMENTS

| | | |
|---|---|---|
| 2016/0213483 A1 | 7/2016 | To et al. |
| 2017/0035576 A1 | 2/2017 | Schaller et al. |
| 2017/0156880 A1* | 6/2017 | Halverson ............. A61F 2/0077 |
| 2017/0216049 A1 | 8/2017 | Grotz |
| 2017/0224506 A1 | 8/2017 | Ashley et al. |
| 2018/0092755 A1 | 4/2018 | Lechmann et al. |
| 2018/0125677 A1 | 5/2018 | Burrows-Ownbey et al. |

* cited by examiner

EXPANDING INTERBODY SPACERS

CROSS-REFERENCE TO RELATED APPLICATIONS

This application claims the benefit of U.S. Provisional Application No. 62/640,555, filed Mar. 8, 2018, U.S. Provisional Application No. 62/736,924, filed Sep. 26, 2018, and U.S. Provisional Application No. 62/751,432, filed Oct. 26, 2018, each of which is incorporated herein by reference in its entirety for all it discloses.

BACKGROUND OF THE INVENTION

1. Field of the Invention

The present invention relates to spinal implants, and more particularly to expanding interbody spacers for use in spinal fusion procedures.

2. Background and Related Art

In certain spinal fusion procedures, an interbody spacer is used to support and stabilize the spine while the fusion occurs. There are different types of procedures in which different types of access are used to place the interbody spacer. These types of access include transforaminal lumbar interbody fusion (TILF), posterior lumbar interbody fusion (PLIF) and lateral lumbar interbody fusion (LLIF) procedures. In many instances, surgical access to the interbody space is limited, and it therefore becomes difficult to place large, supportive interbody spacers through the limited access sites.

To address this difficulty, to reduce the amount of trialing needed, and to reduce the force of insertion needed, expanding interbody spacers have been used for stabilizing the spine and encouraging fusion of adjacent vertebrae. Existing expanding interbody spacers have remaining problems, however. Existing spacers may induce subsidence through excessive stiffness, localized over-loading, or by requiring procedural weakening of the vertebral endplates (e.g., by excessive rasping). Additionally, existing spacers may create regions of stress shielding that locally inhibit bone formation and fusion. Finally, most existing spacers do not have an optimal pore size for bone on-growth and bone ingrowth or through-growth.

BRIEF SUMMARY OF THE INVENTION

Implementation of the invention provides improved expanding interbody technology that overcomes many of the problems with current interbody spacers. Expanding interbody technology is improved by the use of designs and/or materials that allow for improved conformance of the interbody spacer to the vertebral endplates, thereby reducing rasping requirements and localized overloading that may lead to subsidence. Expanding interbody technology is also improved by the use of designs and/or materials that better match the stiffness of bone and allow for better load sharing. This encourages better bone formation and reduced stress shielding.

Expanding interbody technology is also improved by the use of designs and/or materials with pore sizes appropriate to encourage bone on-growth, ingrowth, and/or through-growth. Expanding interbody technology is further improved by better allowing for correction of spinal alignment. The expansion mechanism may be used to control the amount of force exerted on the spine.

Implementations of the expandable interbody spacers have a correct stiffness to more-closely match the stiffness of bone. Implementations of the spinal interbody spacer also have the ability to conform to endplate shape. The correct stiffness and conformability of the spinal interbody spacers may each contribute to minimizing subsidence, endplate fracture, and stress shielding. Additionally, interbody spacers in accordance with implementations of the invention, being expandable, reduces carrying/inventory costs by reducing the number of heights offered. This also reduces the need for trialing for the surgeon.

The improved expanding interbody technology also has application outside of spinal implants. Examples of non-spinal applications include radially expanding femoral stems and hip and knee replacements.

According to implementations of the invention, an expandable interbody spacer includes a first endplate surface located on a first side of the spacer and adapted to contact a vertebral endplate surface of a first vertebral body, a second endplate surface located on a second, opposed, side of the spacer and adapted to contact a vertebral endplate surface of a second, opposed, vertebral body and an expansion mechanism adapted to selectively apply a distracting force between the first endplate surface and the second endplate surface, whereby actuation of the expansion mechanism causes the spacer to transition between a compressed insertion configuration to an expanded fusion configuration. The first endplate surface and the second endplate surface are conformable to the first vertebral endplate surface and the second vertebral endplate surface.

In some implementations, the first endplate surface is substantially contiguous and the second endplate surface is substantially contiguous. In some implementations, the first endplate surface and the second endplate surface include a deformable material. In some implementations, the first endplate surface and the second endplate surface are each formed from a plurality of discrete and separate surface-forming elements. In some implementations, the first endplate surface and the second endplate surface include a surface having a porosity adapted to promote bone on-growth and through-growth onto and through the spacer.

In some implementations, a structure of the spacer extending between the first endplate surface and the second endplate surface includes a stiffness substantially equivalent to a stiffness of cortical bone of the first and second vertebral bodies. In some implementations, loads applied to the first endplate surface are transmitted to the second endplate surface substantially without being distributed to a portion of the spacer having a stiffness greater than twice the stiffness of cortical bone of the first and second vertebral bodies. In some implementations, a shape-locking mechanism is adapted to lock the spacer in the expanded fusion configuration, wherein the shape-locking mechanism operates independently of actuation of the expansion mechanism.

According to further implementations of the invention, an expandable interbody spacer includes a first endplate surface located on a first side of the spacer and adapted to contact a vertebral endplate surface of a first vertebral body, a second endplate surface located on a second, opposed, side of the spacer and adapted to contact a vertebral endplate surface of a second, opposed, vertebral body, and an expansion mechanism adapted to selectively apply a distracting force between the first endplate surface and the second endplate surface, whereby actuation of the expansion mechanism causes the spacer to transition between a compressed insertion configuration to an expanded fusion configuration. A structure of the spacer extending between the first endplate surface and the second endplate surface has a stiffness substantially equivalent to a stiffness of cortical bone of the first and second vertebral bodies.

In some implementations, the first endplate surface and the second endplate surface are conformable to the first vertebral endplate surface and the second vertebral endplate surface. In some implementations, the first endplate surface and the second endplate surface are each formed from a plurality of discrete and separate surface-forming elements. In some implementations, the first endplate surface and the second endplate surface include a surface having a porosity adapted to promote bone on-growth and through-growth onto and through the spacer. In some implementations, a structure of the spacer extending between the first endplate surface and the second endplate surface includes a porosity adapted to promote bone through-growth through the spacer.

In some implementations, loads applied to the first endplate surface are transmitted to the second endplate surface substantially without being distributed to a portion of the spacer having a stiffness greater than twice the stiffness of cortical bone of the first and second vertebral bodies. In some implementations, a shape-locking mechanism is adapted to lock the spacer in the expanded fusion configuration, wherein the shape-locking mechanism operates independently of actuation of the expansion mechanism.

According to alternate implementations of the invention, an expandable interbody spacer includes a first endplate surface located on a first side of the spacer and adapted to contact a vertebral endplate surface of a first vertebral body, a second endplate surface located on a second, opposed, side of the spacer and adapted to contact a vertebral endplate surface of a second, opposed, vertebral body, and an expansion mechanism adapted to selectively apply a distracting force between the first endplate surface and the second endplate surface, whereby actuation of the expansion mechanism causes the spacer to transition between a compressed insertion configuration to an expanded fusion configuration. The first endplate surface and the second endplate surface and a structure extending between the first endplate surface and the second endplate surface all have a porosity adapted to promote bone on-growth and through-growth through the spacer.

In some implementations, the porosity consists essentially of pores no larger than 650 microns. In some implementations, the porosity consists essentially of pores no larger than 500 microns. In some implementations, the first endplate surface and the second endplate surface are conformable to the first vertebral endplate surface and the second vertebral endplate surface. In some implementations, the first endplate surface and the second endplate surface are each formed from a plurality of discrete and separate surface-forming elements.

According to still other implementations of the invention, an expandable interbody spacer includes a first endplate surface located on a first side of the spacer and adapted to contact a vertebral endplate surface of a first vertebral body, a second endplate surface located on a second, opposed, side of the spacer and adapted to contact a vertebral endplate surface of a second, opposed, vertebral body, and an expansion mechanism adapted to selectively apply a distracting force between the first endplate surface and the second endplate surface, whereby actuation of the expansion mechanism causes the spacer to transition between a compressed insertion configuration to an expanded fusion configuration. Loads applied to the first endplate surface are transmitted to the second endplate surface substantially without being distributed to a portion of the spacer having a stiffness greater than twice the stiffness of cortical bone of the first and second vertebral bodies, thereby minimizing a risk of post-implant subsidence.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
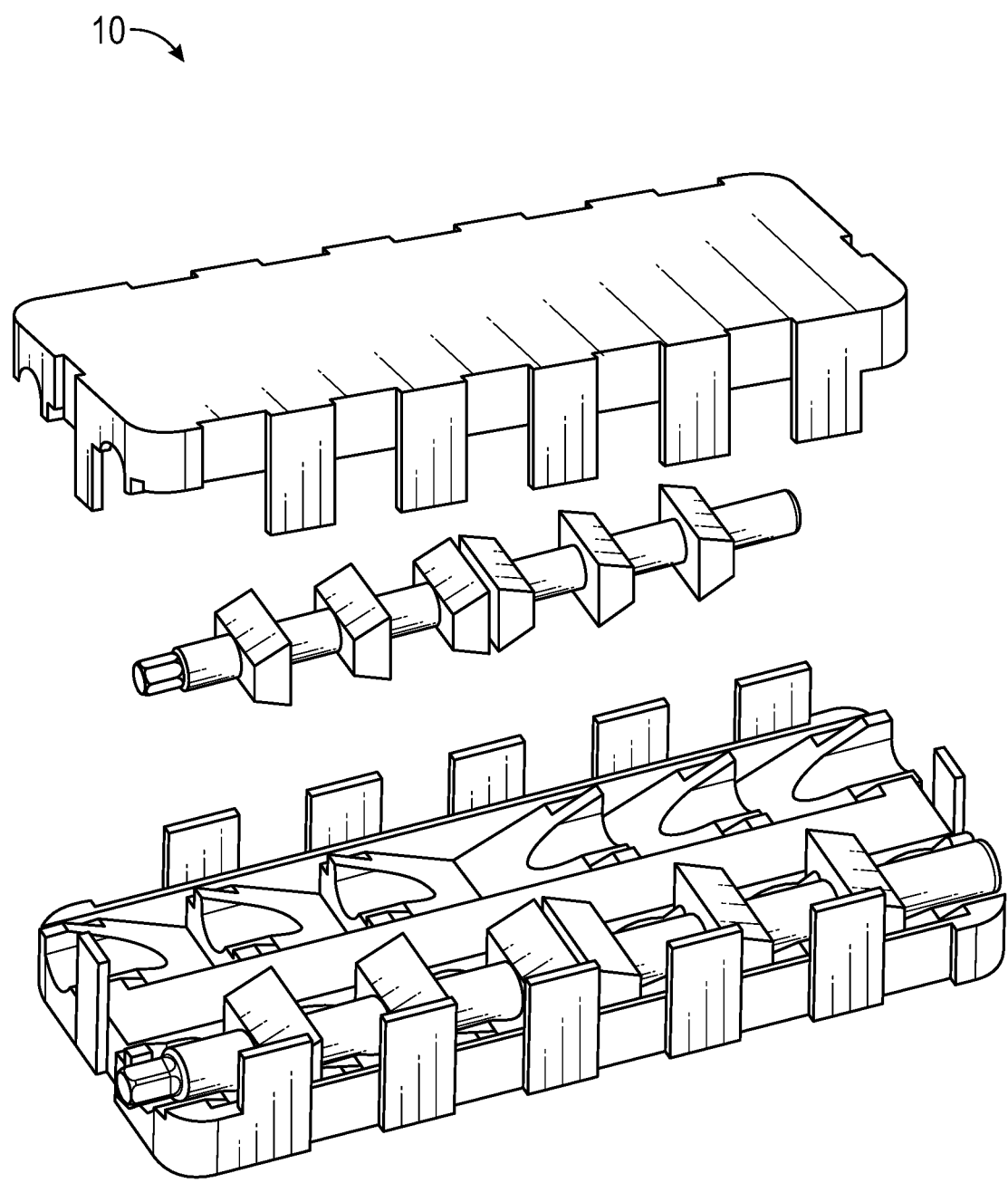
FIG. 1 shows an embodiment of an expandable interbody spacer.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide improved expanding interbody technology that overcomes many of the problems with current interbody spacers. Expanding interbody technology is improved by the use of designs and/or materials that allow for improved conformance of the interbody spacer to the vertebral endplates, thereby reducing rasping requirements and localized overloading that may lead to subsidence. Expanding interbody technology is also improved by the use of designs and/or materials that better match the stiffness of bone and allow for better load sharing. This encourages better bone formation and reduced stress shielding.

Expanding interbody technology is also improved by the use of designs and/or materials with pore sizes appropriate to encourage bone on-growth, ingrowth, and/or through-growth. Expanding interbody technology is further improved by better allowing for correction of spinal alignment. The expansion mechanism may be used to control the amount of force exerted on the spine.

Embodiments of the expandable interbody spacers have a correct stiffness to more-closely match the stiffness of bone. Embodiments of the spinal interbody spacer also have the ability to conform to endplate shape. The correct stiffness and conformability of the spinal interbody spacers may each contribute to minimizing subsidence, endplate fracture, and stress shielding. Additionally, interbody spacers in accordance with embodiments of the invention, being expandable, reduces carrying/inventory costs by reducing the number of heights offered. This also reduces the need for trialing for the surgeon.

The improved expanding interbody technology also has application outside of spinal implants. Examples of non-spinal applications include radially expanding femoral stems and hip and knee replacements.

According to embodiments of the invention, an expandable interbody spacer includes a first endplate surface located on a first side of the spacer and adapted to contact a vertebral endplate surface of a first vertebral body, a second endplate surface located on a second, opposed, side of the spacer and adapted to contact a vertebral endplate surface of a second, opposed, vertebral body and an expansion mechanism adapted to selectively apply a distracting force between the first endplate surface and the second endplate surface, whereby actuation of the expansion mechanism causes the spacer to transition between a compressed insertion configuration to an expanded fusion configuration. The first endplate surface and the second endplate surface are conformable to the first vertebral endplate surface and the second vertebral endplate surface.

In some embodiments, the first endplate surface is substantially contiguous and the second endplate surface is substantially contiguous. In some embodiments, the first endplate surface and the second endplate surface include a deformable material. In some embodiments, the first endplate surface and the second endplate surface are each formed from a plurality of discrete and separate surface-forming elements. In some embodiments, the first endplate surface and the second endplate surface include a surface having a porosity adapted to promote bone on-growth and through-growth onto and through the spacer.

In some embodiments, a structure of the spacer extending between the first endplate surface and the second endplate surface includes a stiffness substantially equivalent to a stiffness of cortical bone of the first and second vertebral bodies. In some embodiments, loads applied to the first endplate surface are transmitted to the second endplate surface substantially without being distributed to a portion of the spacer having a stiffness greater than twice the stiffness of cortical bone of the first and second vertebral bodies. In some embodiments, a shape-locking mechanism is adapted to lock the spacer in the expanded fusion configuration, wherein the shape-locking mechanism operates independently of actuation of the expansion mechanism.

According to further embodiments of the invention, an expandable interbody spacer includes a first endplate surface located on a first side of the spacer and adapted to contact a vertebral endplate surface of a first vertebral body, a second endplate surface located on a second, opposed, side of the spacer and adapted to contact a vertebral endplate surface of a second, opposed, vertebral body, and an expansion mechanism adapted to selectively apply a distracting force between the first endplate surface and the second endplate surface, whereby actuation of the expansion mechanism causes the spacer to transition between a compressed insertion configuration to an expanded fusion configuration. A structure of the spacer extending between the first endplate surface and the second endplate surface has a stiffness substantially equivalent to a stiffness of cortical bone of the first and second vertebral bodies.

In some embodiments, the first endplate surface and the second endplate surface are conformable to the first vertebral endplate surface and the second vertebral endplate surface. In some embodiments, the first endplate surface and the second endplate surface are each formed from a plurality of discrete and separate surface-forming elements. In some embodiments, the first endplate surface and the second endplate surface include a surface having a porosity adapted to promote bone on-growth and through-growth onto and through the spacer. In some embodiments, a structure of the spacer extending between the first endplate surface and the second endplate surface includes a porosity adapted to promote bone through-growth through the spacer.

In some embodiments, loads applied to the first endplate surface are transmitted to the second endplate surface substantially without being distributed to a portion of the spacer having a stiffness greater than twice the stiffness of cortical bone of the first and second vertebral bodies. In some embodiments, a shape-locking mechanism is adapted to lock the spacer in the expanded fusion configuration, wherein the shape-locking mechanism operates independently of actuation of the expansion mechanism.

According to alternate embodiments of the invention, an expandable interbody spacer includes a first endplate surface located on a first side of the spacer and adapted to contact a vertebral endplate surface of a first vertebral body, a second endplate surface located on a second, opposed, side of the spacer and adapted to contact a vertebral endplate surface of a second, opposed, vertebral body, and an expansion mechanism adapted to selectively apply a distracting force between the first endplate surface and the second endplate surface, whereby actuation of the expansion mechanism causes the spacer to transition between a compressed insertion configuration to an expanded fusion configuration. The first endplate surface and the second endplate surface and a structure extending between the first endplate surface and the second endplate surface all have a porosity adapted to promote bone on-growth and through-growth through the spacer.

In some embodiments, the porosity consists essentially of pores no larger than 650 microns. In some embodiments, the porosity consists essentially of pores no larger than 500 microns. In some embodiments, the first endplate surface and the second endplate surface are conformable to the first vertebral endplate surface and the second vertebral endplate surface. In some embodiments, the first endplate surface and the second endplate surface are each formed from a plurality of discrete and separate surface-forming elements.

According to still other embodiments of the invention, an expandable interbody spacer includes a first endplate surface located on a first side of the spacer and adapted to contact a vertebral endplate surface of a first vertebral body, a second endplate surface located on a second, opposed, side of the spacer and adapted to contact a vertebral endplate surface of a second, opposed, vertebral body, and an expansion mechanism adapted to selectively apply a distracting force between the first endplate surface and the second endplate surface, whereby actuation of the expansion mechanism causes the spacer to transition between a compressed insertion configuration to an expanded fusion configuration. Loads applied to the first endplate surface are transmitted to the second endplate surface substantially without being distributed to a portion of the spacer having a stiffness greater than twice the stiffness of cortical bone of the first and second vertebral bodies, thereby minimizing a risk of post-implant subsidence.

Figure 2:
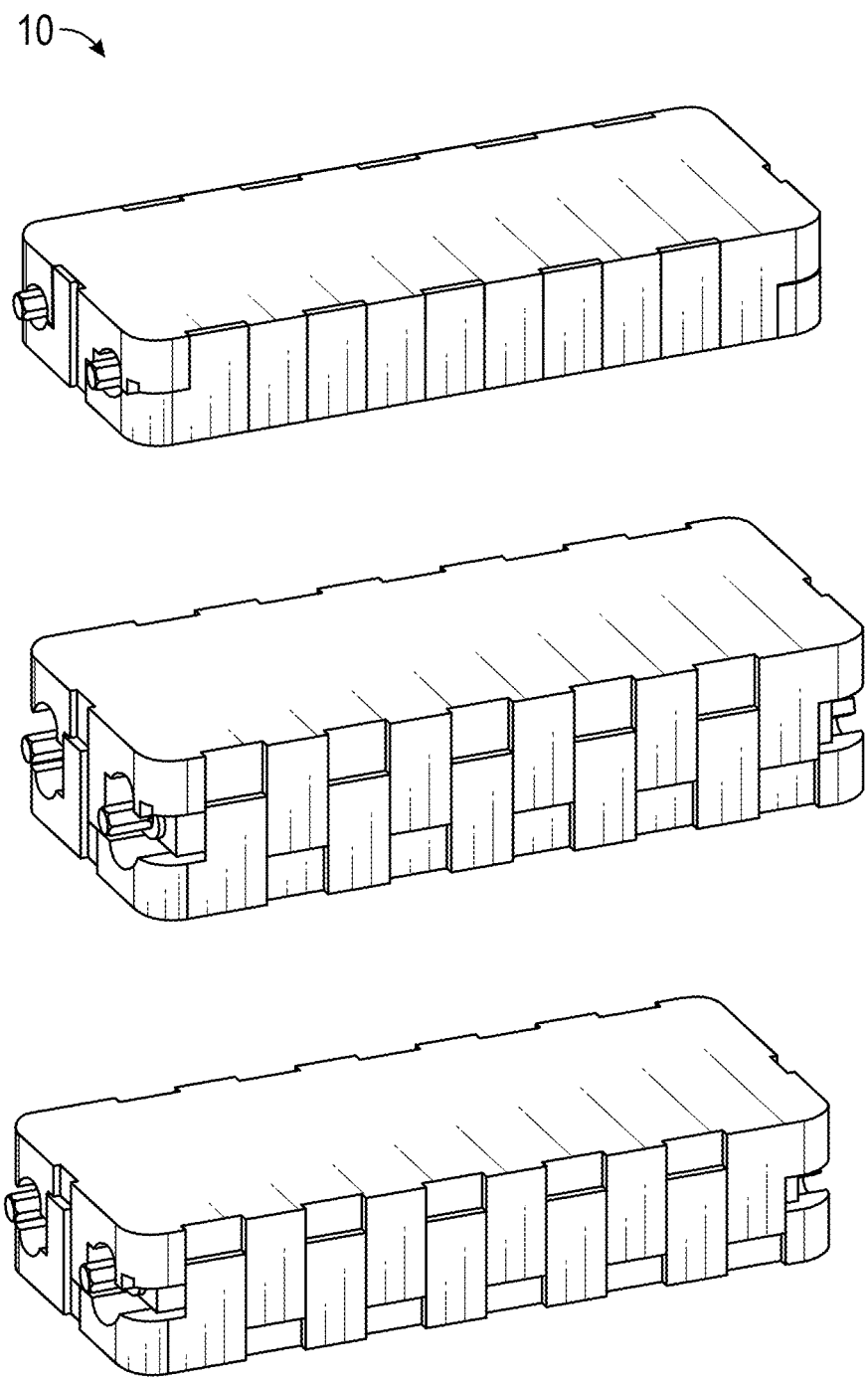
FIG. 2 shows views of the spacer of FIG. 1 in several positions.

FIGS. 1 and 2 illustrate a twelve-wedge design of an embodiment of an expandable interbody spacer 10. In FIG. 1, the spacer 10 is shown in partially exploded view, while in FIG. 2, the spacer 10 is shown collapsed (top), fully expanded (middle), and partially expanded (bottom). The spacer 10 includes twelve ramps (A) that are incorporated into end plates (D). A lifting assembly is created by installing opposing wedges (B and C) on a screw (E), with one half of the screw having a right-hand thread and the other half having a left-hand thread such that when the screw is rotated, the two groups of wedges either move apart or move towards each other. The assembly consists of two end plates and two lifting assemblies.

With a lateral placement, one screw controls height on the anterior side of the implant, and the other controls height at the posterior side of the implant. By adjusting the heights differentially, it is possible to give the implant lordosis. The auxiliary tab features (F) around the perimeter of the end plates (D) keep the end plates aligned, while still being flexible enough to allow differential adjustment. They may also have detent features that allow the end plates to snap together and limit the expansion to the intended range.

Rotating the screws moves the implant from the collapsed to expanded state. If necessary, the screws can be counter-rotated which will allow the implant to collapse. While many existing designs utilize screw-driven wedges or ramps, there are several important differences in this design. First, the end plates structure and/or material gives them a modulus similar to bone, as well as a little bit of compliance. The end plate material may be a structure similar to that disclosed in U.S. patent application Ser. No. 15/372,290, incorporated herein by reference in its entirety for all it discloses, or it may be of another topology or material. Second, the two screws lift independently, and additionally, because the screws are not constrained to the end plates, the opposing wedge groups (B and C) are not forced to lift in equal amounts. If one side of the implant experiences increased load at early contact, the opposite side will rise until the load is balance. Thus, four zones of lifting are created to better conform to the endplate shape and reduce local overload, as shown in the bottom illustration of FIG. 2. Third, the wedges may be made of a slightly compliant material to allow the implant to flex and spread out the load. Fourth, although the simplified diagrams presented show smooth outer surfaces, in reality, the bone-contacting surfaces would have a more open structure giving proper pore size for bone formation and ongrowth.

Figure 3:
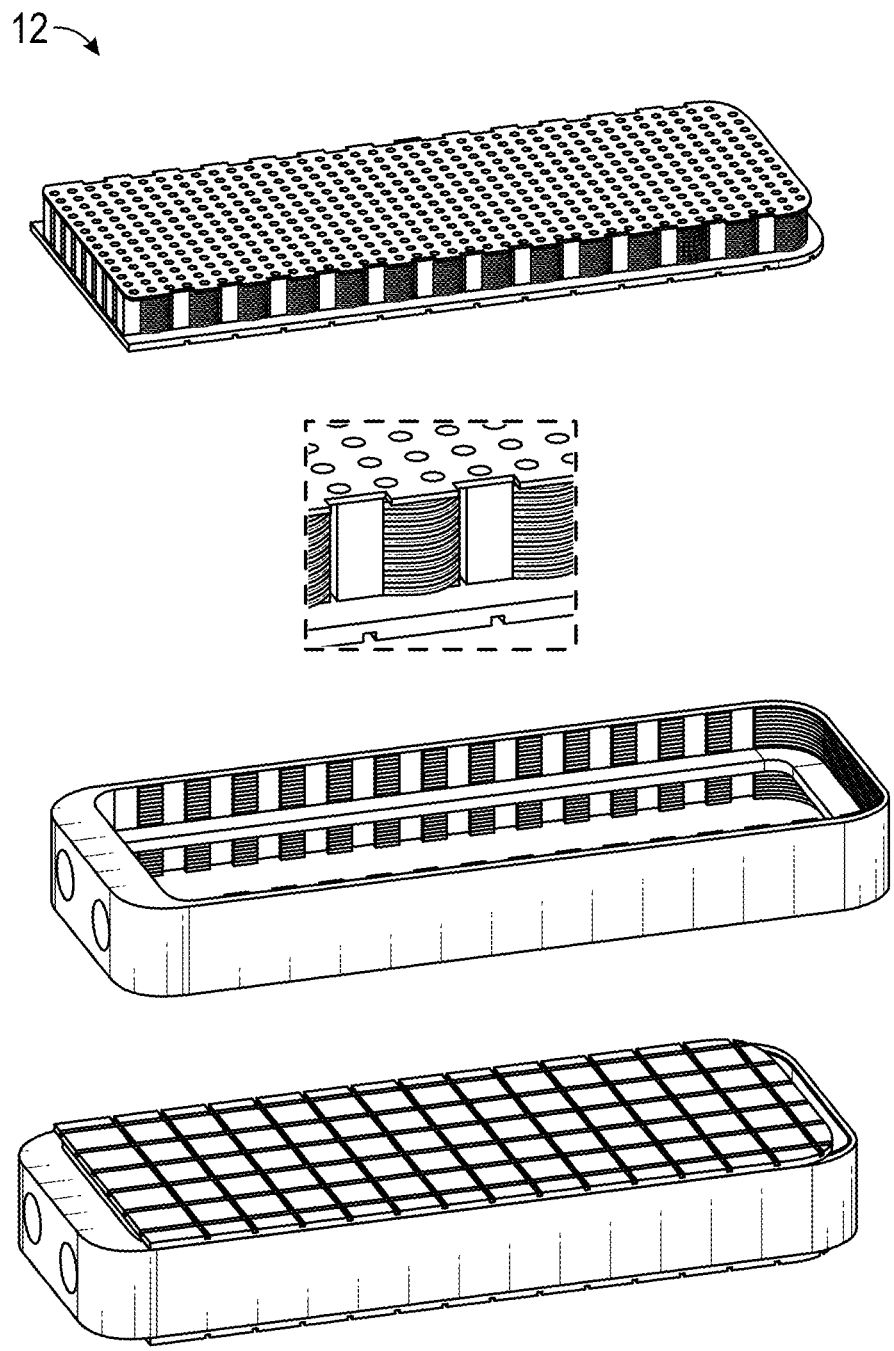
FIG. 3 shows an alternate embodiment of an expandable interbody spacer.
Figure 4:
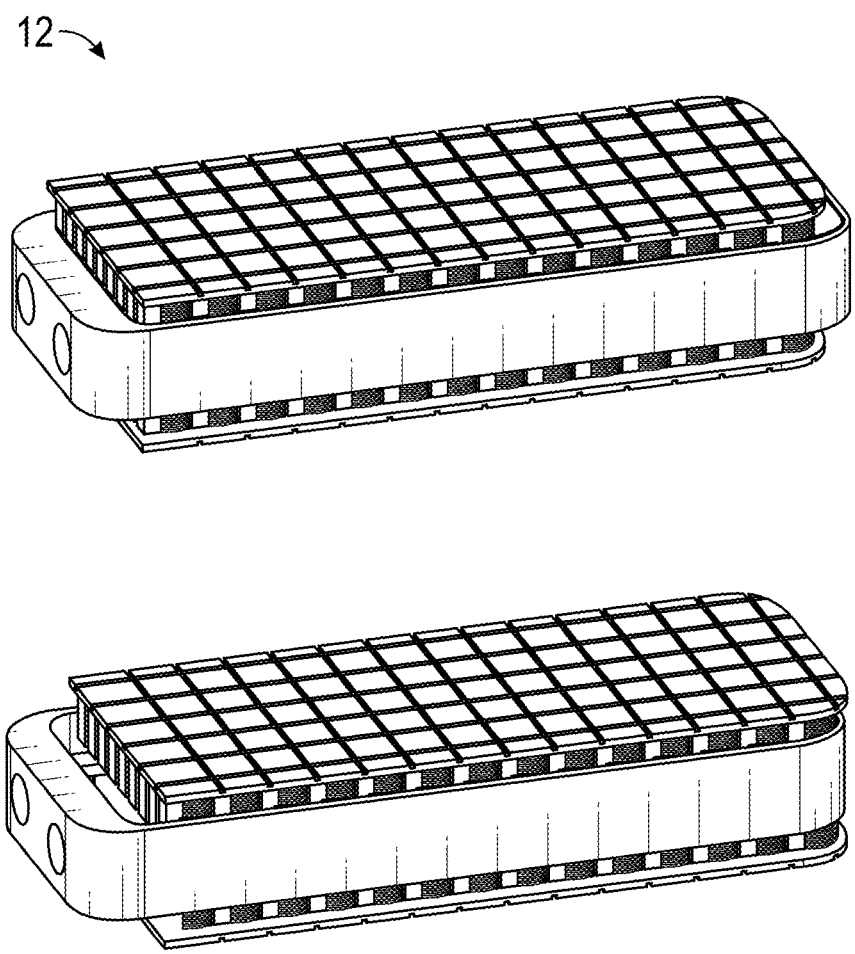
FIG. 4 shows views of the embodiment of FIG. 3.

FIGS. 3 and 4 illustrate a border frame design of an alternate embodiment of an expandable interbody spacer 12. FIG. 3 shows an exploded view of the spacer 12 and a view of the spacer 12 in a collapsed state, while FIG. 4 shows the spacer 12 in an expanded position (top) as well as an expanded and locked position (bottom). In this embodiment, an end plate (A) is created from a compliant material/structure combination to mimic the stiffness of bone and promote even load distribution. Sides of the endplate have alternating sets of teeth (B). An external frame (C) has alternating sets of teeth around its inside edge (E) as well as access (D) for lifting and locking implements.

Two end-plates are inserted in the frame to create a collapsed assembly (F) (bottom of FIG. 3). The endplates have some kind of grooves/articulation points (G) such that they are not required to stay planar upon contacting the vertebral endplates. The teeth in the endplates are offset from the teeth in the frame such that the endplates can travel within the frame.

A pressure-based lift mechanism (e.g. kyphoplasty-type balloon or similar) expands the endplates out until they make contact with the endplates and provide the desired distraction with a quasi-uniform pressure distribution on the bone surface (H) (top of FIG. 4). The frame is pulled back around the endplates such that the teeth in the endplates engage the teeth in the frame, locking the endplate to whatever shape best matches the bone (I) (bottom of FIG. 4). The balloon is deflated and withdrawn, and the center of the implant is packed with bone graft material.

Figure 5:
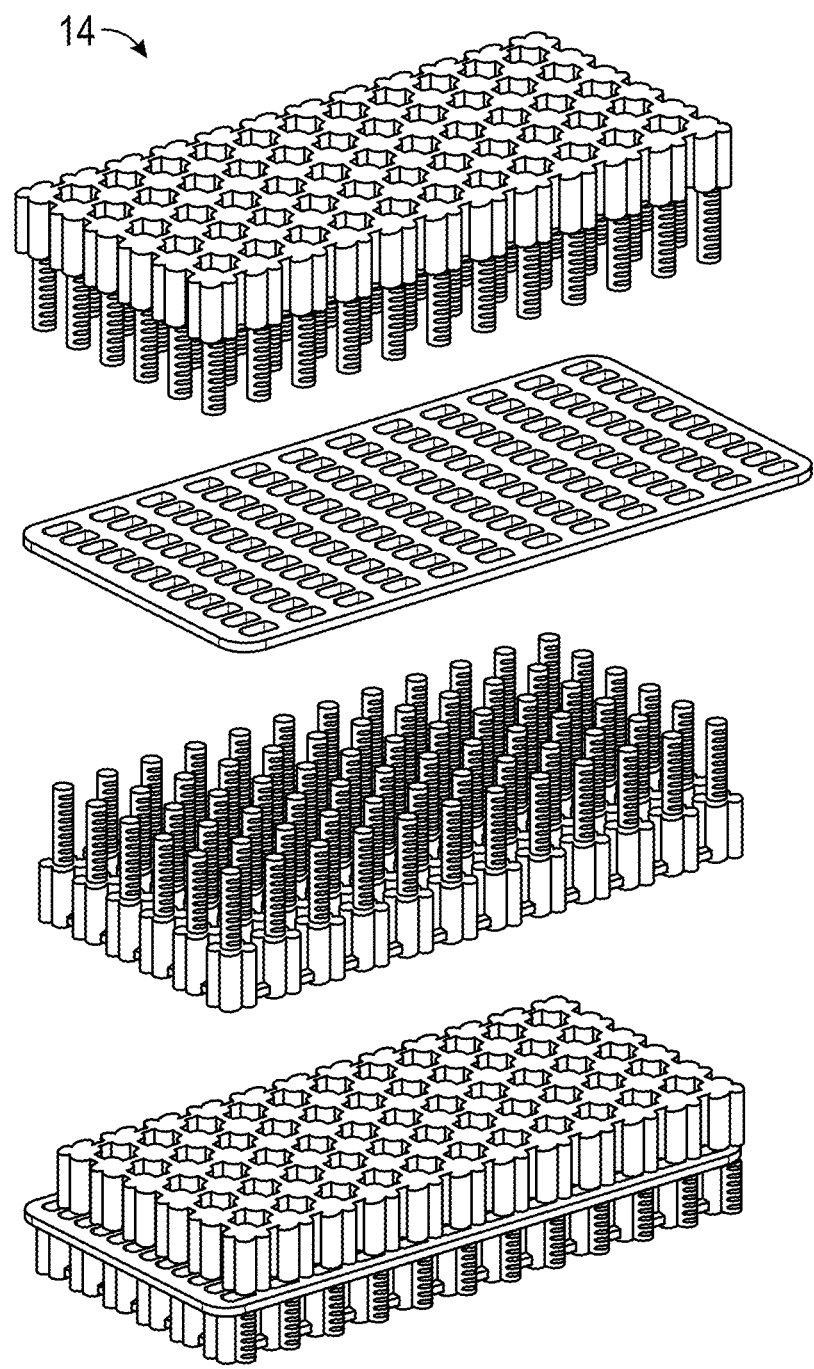
FIG. 5 shows views of an embodiment of an expandable interbody spacer.
Figure 6:
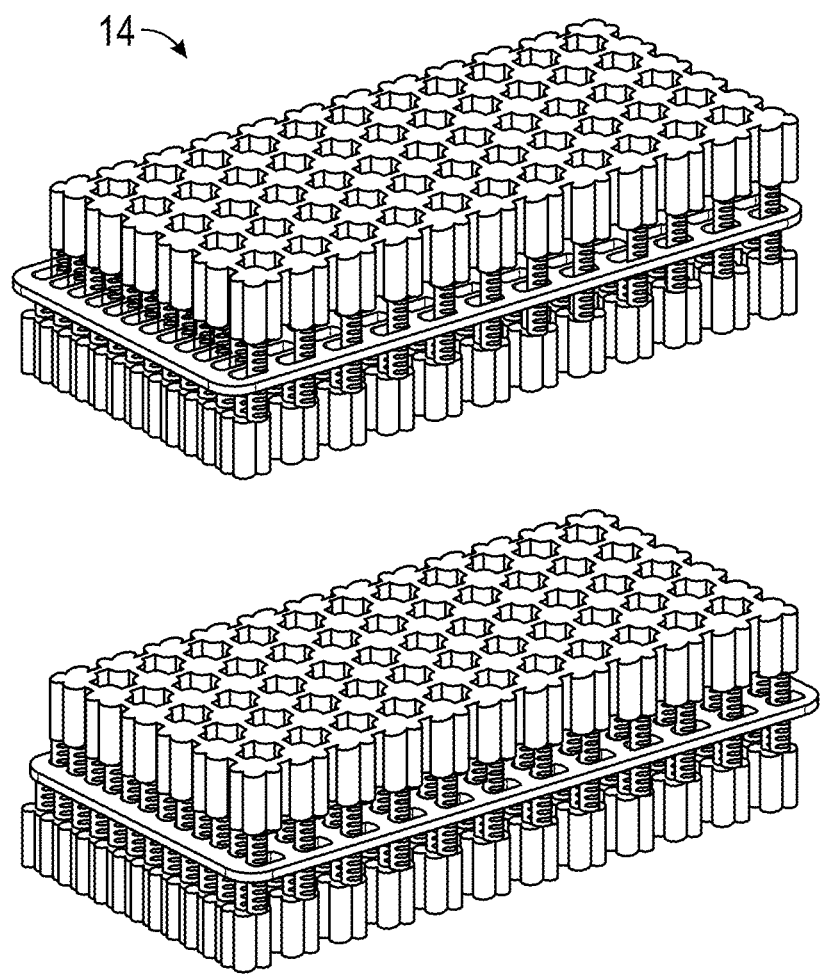
FIG. 6 shows views of the embodiment of FIG. 5.
Figure 14:
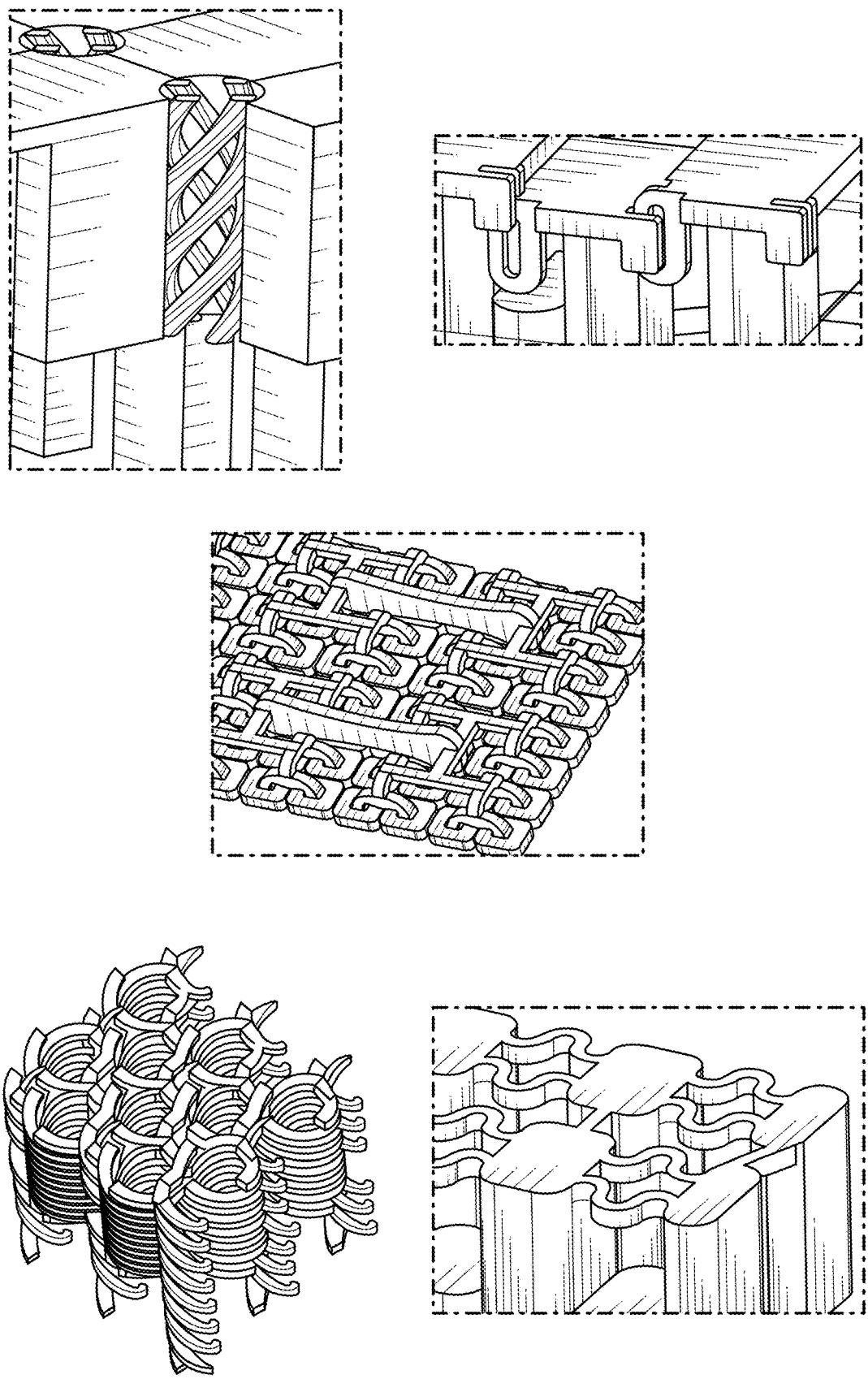
FIG. 14 illustrates various ways in which to create interlocking segments of embodiments of an expandable interbody spacer.
Figure 15:
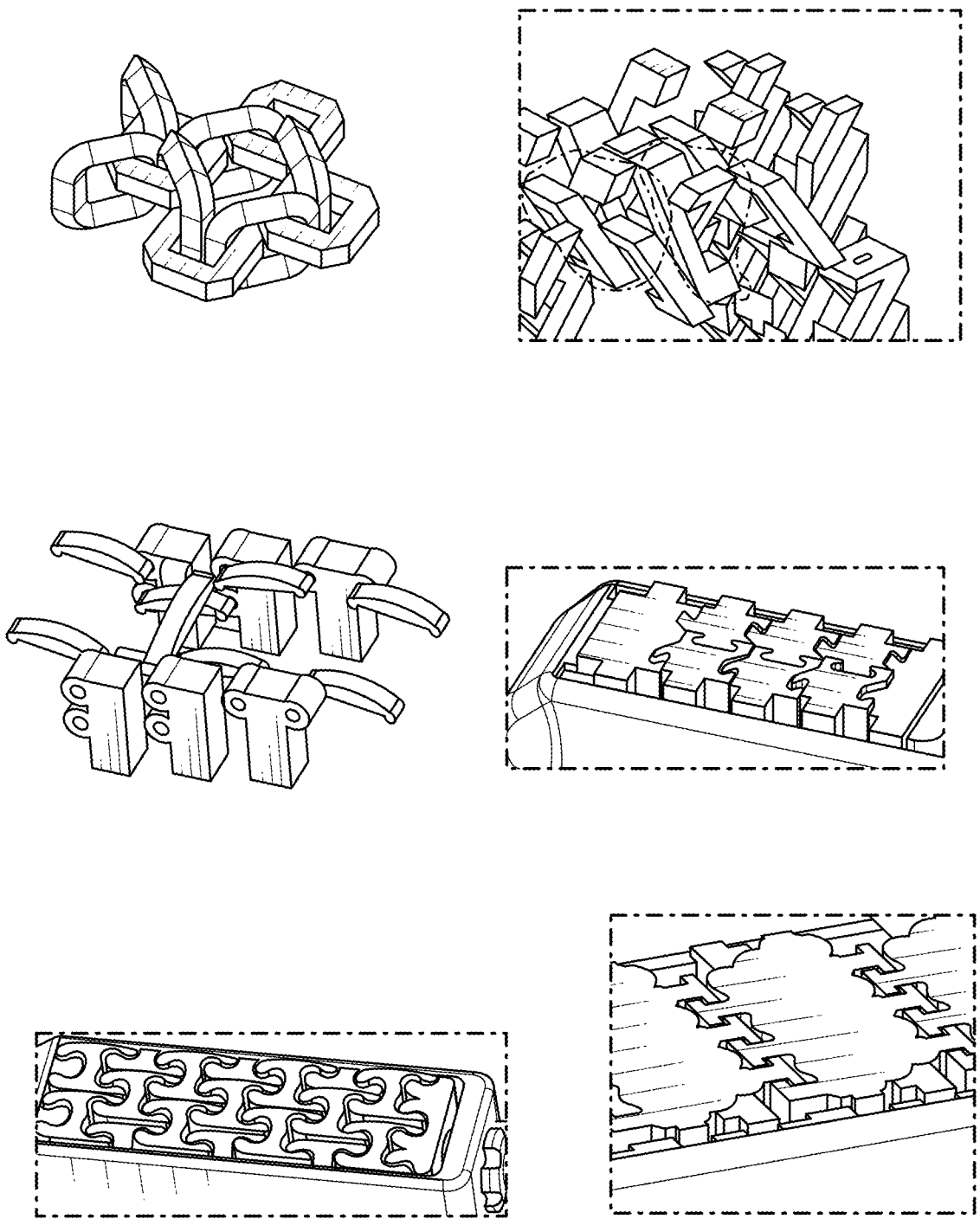
FIG. 15 illustrate alternate ways in which to create interlocking segments of embodiments of an expandable interbody spacer.

FIGS. 5 and 6 illustrate a bed-of-nails design of an alternate embodiment of an expandable interbody spacer 14. FIG. 14 shows an exploded view of the spacer 14 as well as an assembled spacer 14 in a collapsed state. FIG. 15 shows the spacer 14 in an expanded state (top) as well as in an expanded and locked state (bottom). In this embodiment, a group of compliant pillars fitted with toothed stems on the underside (inwardly-directed side) and joined by surface webbing creates an endplate (A). The stems themselves may be a relatively compliant structure, or larger or smaller dimensions than that shown.

A locking plate (B) has a series of slots to accept the toothed stems of the upper endplate (A) and the lower endplate (C) and create an initial assembly (D). The locking plate (B) could be replaced by any other structure having the ability to lock to the stems, and ideally, the locking structure itself would have a compliance similar to that of bone to prevent load short-circuiting within the implant. The locking plate may be set up such that the toothed stems have a ratcheting action.

The implant is introduced into the disc space and expanded (E) to provide distraction (top of FIG. 6). The compliance of the end plates allows them to distribute load and conform to the endplates. Expansion may be accomplished by ramps/screws/cams/inflatable devices, etc. The locking plate is moved within the endplates to lock the teeth at the final height (F) (bottom of FIG. 6). The expanding device may be removed if necessary and the implant packed with additional bone graft. If the expanding device is incorporated into the locking plate, or if the locking plate is replaced by a different mechanism (e.g. RH/LH screw), then it may remain as an integral part of the implant.

Figure 7:
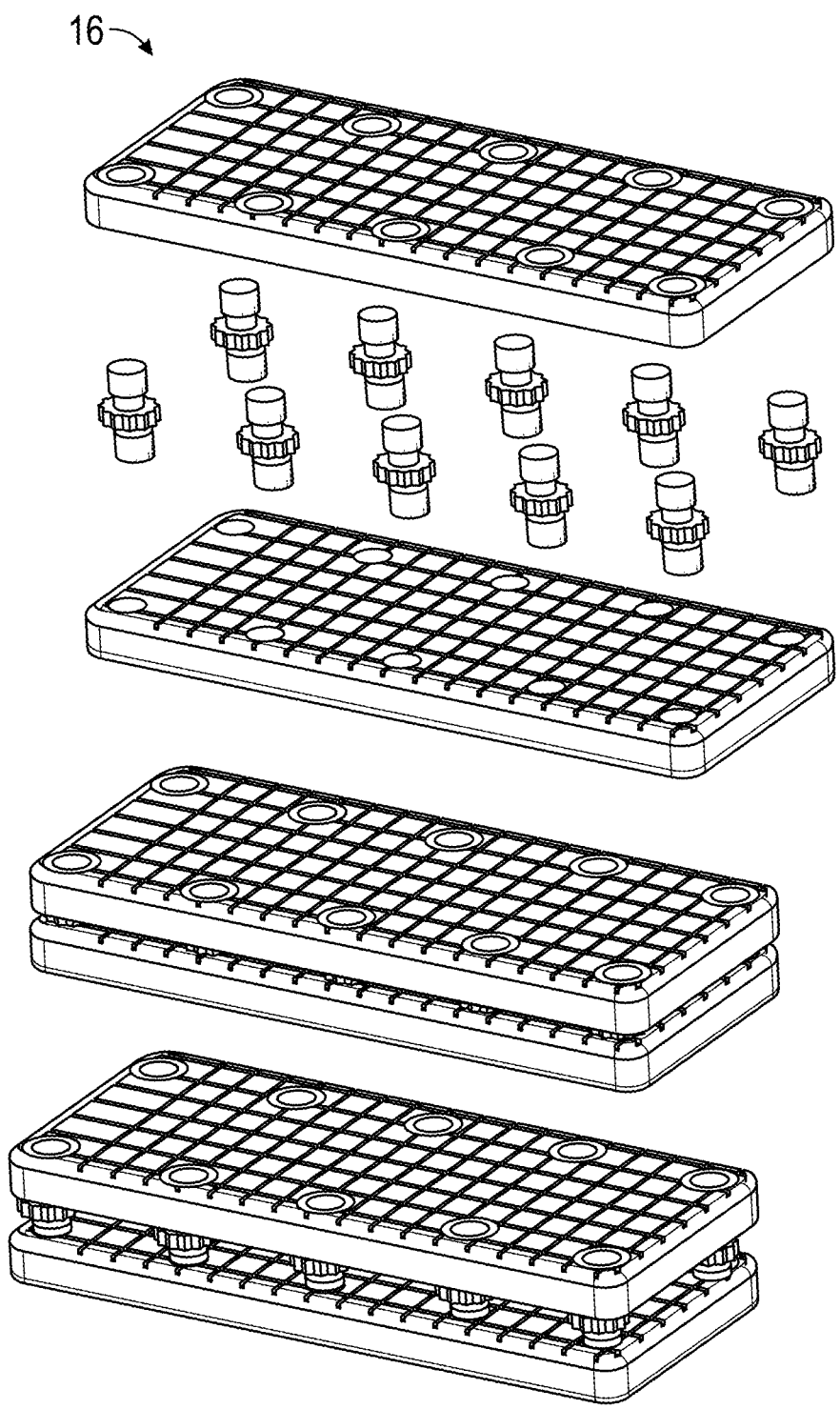
FIG. 7 shows views of an embodiment of an expandable interbody spacer.

FIG. 7 illustrates a multi-screw-jack design of an alternate embodiment of an expandable interbody spacer 16. An exploded spacer 16 is shown at the top of FIG. 7, an assembled spacer 16 is shown in the middle in a collapsed state, and at the bottom of FIG. 7 the spacer 16 is shown in an expanded state. In this embodiment, an upper (A) and lower (C) endplate are created from a compliant material/structure having a stiffness similar to bone. Articulating grooves or other features allow the endplates to take on a non-planar shape and conform to the vertebral endplate. One endplate has structurally isolated right-hand-threaded holes, while the other has structurally isolated left-hand-threaded holes.

A set of actuating posts (B), which themselves may be solid or of a compliant nature have opposite sides fitted with left and right hand threads to match the endplates and are installed between the endplates. Rotation of an individual actuating post causes local expansion or retraction of the implant to shape the endplate to anatomy. Rotation of all the posts together gives distraction (when expanding) rotation or the anterior or posterior actuating posts adjusts lordosis at the implant level. The implant is shown fully collapsed (D) and fully extended (E).

The design shown uses LH/RH threaded posts as both the actuating and height-maintaining mechanism. It would be possible to use a separate mechanism (scissor/cam/balloon) to perform the lifting and endplate-conforming functions, and then modify the stud to act as a quarter-turn fastener and simply lock the endplates in the final position. The design shown uses two rows of actuating posts. It is possible to use more posts, to couple specific posts (through gears/belts/chains/linkages), to arrange posts non-rectilinearly, etc.

Figure 8:
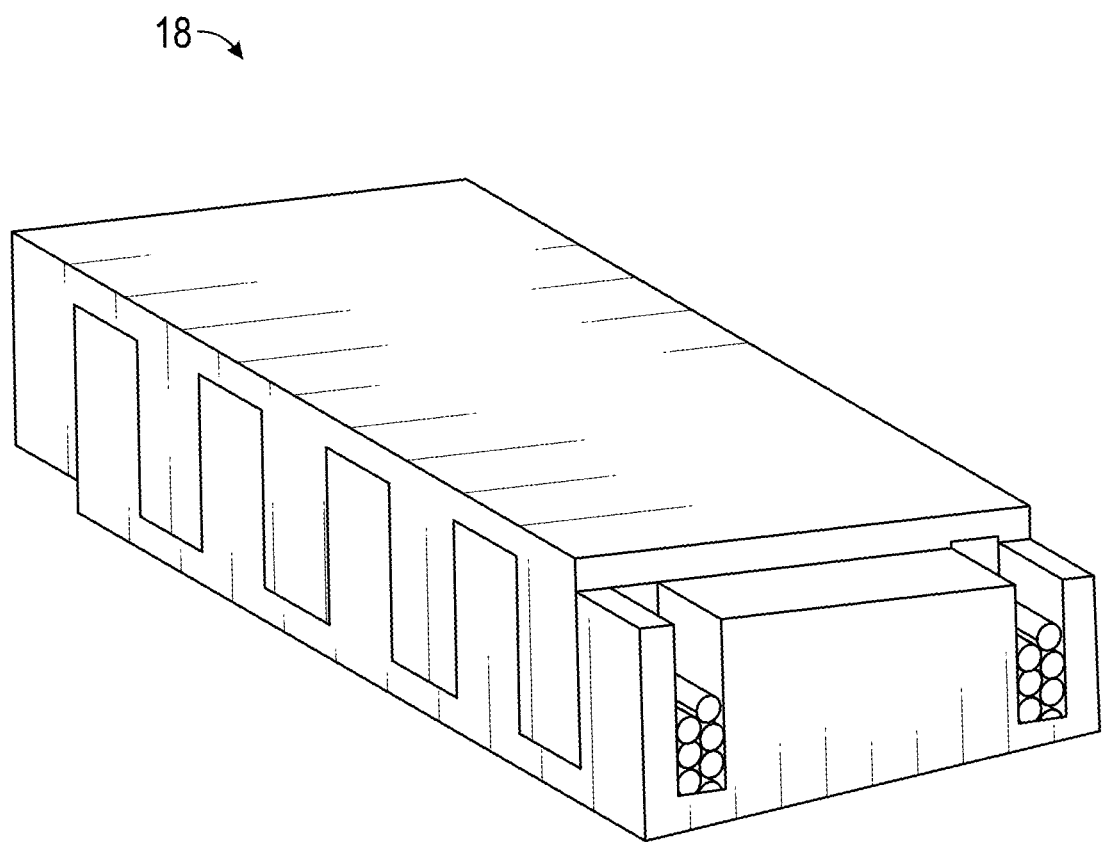
FIG. 8 shows views of an embodiment of an expandable interbody spacer.

FIG. 8 illustrates an incremental lift design of an alternate embodiment of an expandable interbody spacer 18. In this embodiment, two implant halves (made of some kind of compliant/conforming/stiffness-matching material/structure) have channels into which small rods may be inserted to adjust anterior and posterior height separately.

Figure 9:
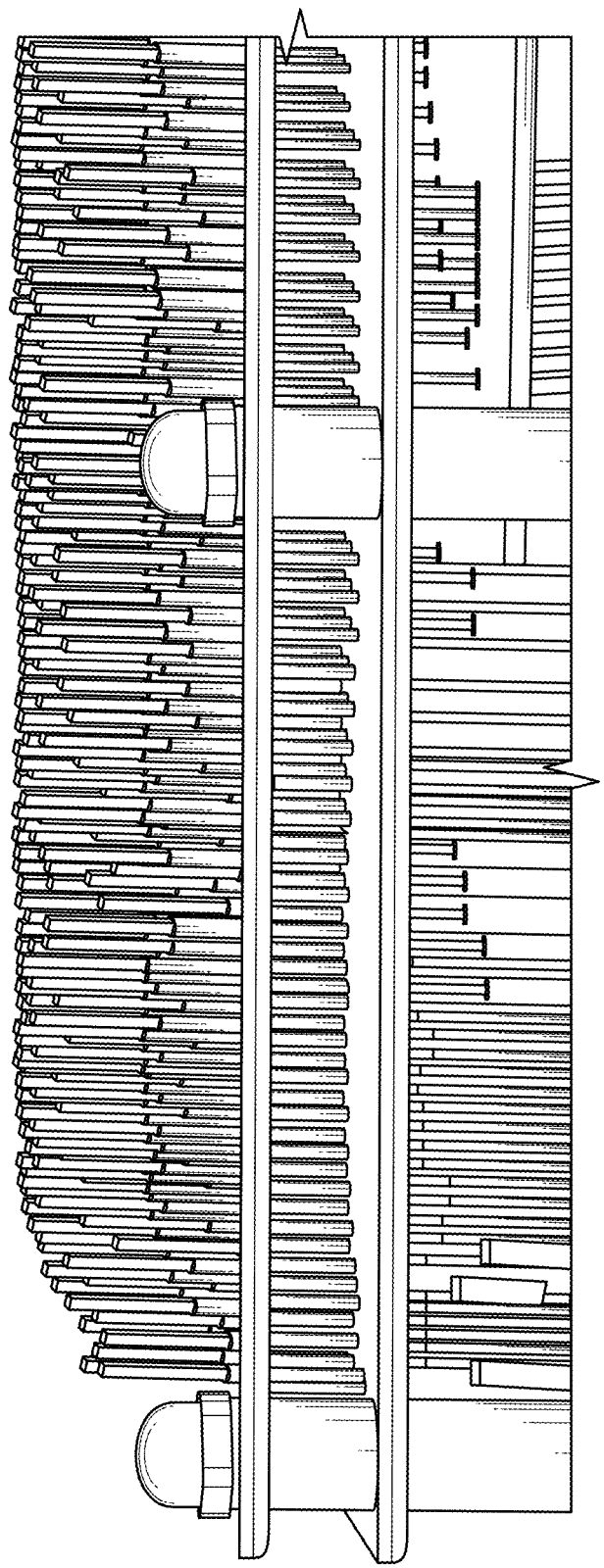
FIG. 9 shows a side view of a spacer mechanism using an inflatable element to cause a plurality of pins to expand and conform to a vertebral endplate.

FIG. 9 illustrates a bladder-and-pin mechanism that may be used with certain embodiments of the expandable interbody spacer. In this mechanism, the spacer is placed within the disc space, and a balloon or bladder disposed within the implant is inflated using a selected fluid (e.g., air, saline, etc.) until the implant's moveable portions (e.g., the pins in this illustrated example or the endplates of other examples) contact and conform to the vertebral endplate surfaces. Once conformance has been achieved, additional pressure supplied to the balloon or bladder distracts the vertebral bodies on either side of the implant. The force that is exerted on the spine may be controlled by the amount of pressure applied through the expansion mechanism.

Accordingly, embodiments of improved expandable interbody spacers include a method, mechanism, or structure of expansion as well as a method, mechanism, or structure promoting retention of the implant. In addition, embodiments of the spacer include one or more of the following novel features: a method mechanism, or structure adapted to conform to the vertebral body on either side of the implant, a stiffness-matched structure, a proper pore size to promote bone on-growth and/or through-growth (pore size smaller than a maximum of 650 microns), and a load/stress-distributing method/mechanism/structure. The designs of the embodiments of FIGS. 1-9 incorporate at least one of the novel features and represent an improvement over existing technology in at least one of these areas. It should be understood that nearly limitless recombination of the design elements, technologies, and building blocks shown and discussed with respect to FIGS. 1-9 or following Figures may be performed while still falling within the scope of this disclosure. The designs specifically illustrated and discussed herein incorporate certain combinations of features, but are not intended to limit the scope of the claimed invention to any particular combination of design features.

Once the spacer is placed, a retention method, mechanism, or structure may be used to retain the spacer in the intervertebral space. Non-limiting examples of methods, mechanisms, or structures that may provide retention include teeth (e.g., disposed on the endplates), friction, an interference fit, binding (e.g., a bar clamp), set screws used to apply lateral loads, cinching a flexible band, and packing the implant with additional material.

It should be noted that many of the design elements discussed herein also represent a potential improvement in the realm of fixed-size interbody spacers.

While certain mechanisms for causing expansion of the expandable spacers have been discussed, such mechanisms are not intended to limit the scope of possible expansion mechanisms and features that may be incorporated into the spacers. By way of further examples, a non-exhaustive list of possible expansion mechanisms include a cam, a screw, a balloon or bladder (the balloon or bladder may be shaped to provide localized loads to certain areas and the balloon and/or structure of the implant may be shaped to provide specific shapes to the expanded spacer), a hydraulic cylinder, a wedge, a ramp, a tapered pin, a scissor, a linkage, solid fluid (e.g. bone graft, ceramic/metallic/polymer/elastomer spheres/powder/slurry), piezoelectrics, a bimetallic element subjected to a temperature differential, a shape memory alloy, a spring, electrostatic force, magnetism, an electroactive polymer, and an expanding chemical reaction.

Figure 10:
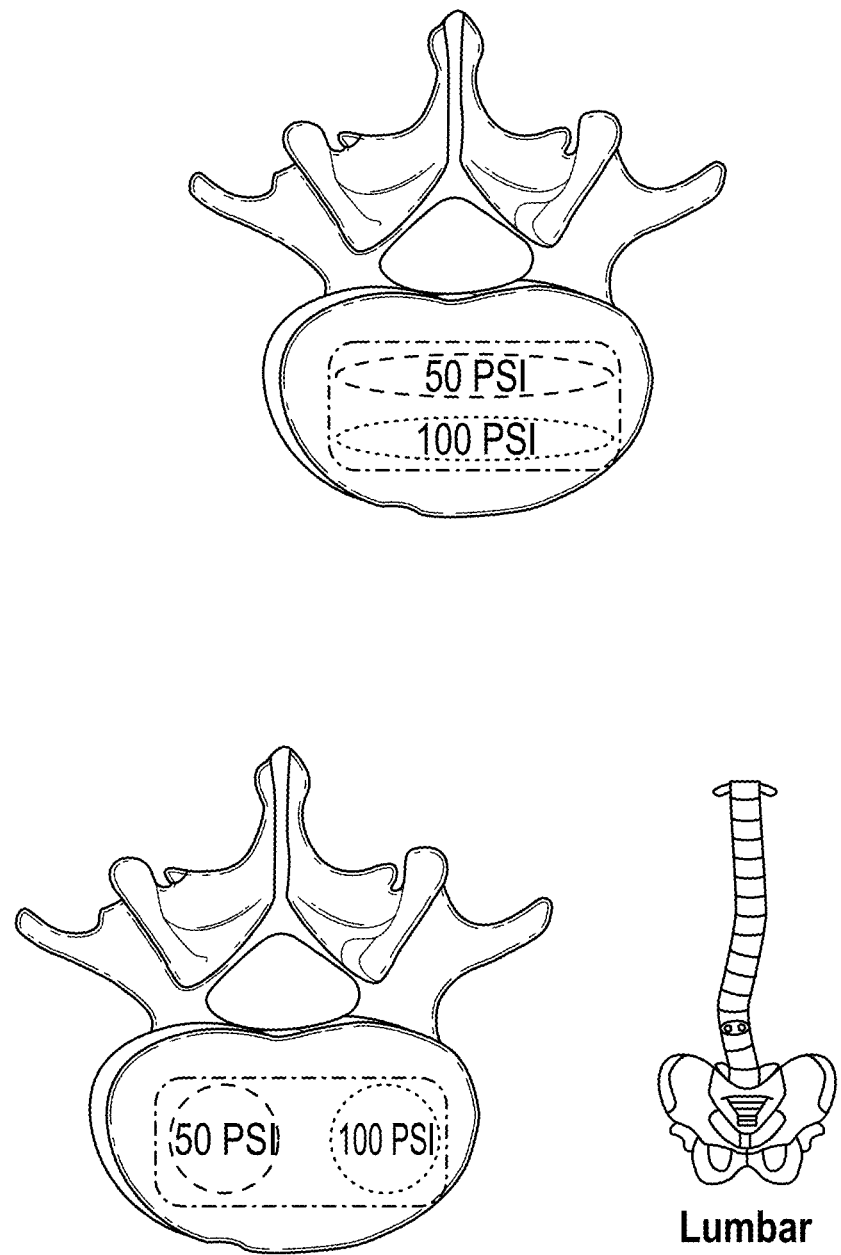
FIG. 10 shows views of applying varying inflation pressures to varying parts of an expandable interbody spacer to provide more force to certain locations of a vertebral endplate.

As illustrated in FIG. 10, expansion mechanisms may be designed to provide more force to one location than another. This directional force differential can be used to treat different conditions. By way of example, as illustrated in the upper portion of FIG. 10, anterior/posterior differences in force may be used to treat kyphosis. As another example, as illustrated in the lower portion of FIG. 10, lateral differences in force may be used to treat scoliosis.

A variety of methods, mechanisms, and/or structures may be used to provide conformance of the endplates of the spacer to the vertebral endplates. By way of non-limiting example, the conformance may be provided by a material configuration as disclosed in U.S. patent application Ser. No. 15/372,290, previously incorporated by reference. As other examples, the implant endplates may include articulated sheets/beds, a compliant jointed bed, individually lifted pins or other components, networked or individual beams/arches/springs/leaf springs/sheet metal forms, a curable material (e.g., a UV-cure polymer/elastomer), a high-deformation material (e.g., super-elastic alloys, a pivoting contact plate, segmented devices, balloon devices, and/or pinned or spherical joint devices (e.g., 2-D tank track). Further examples are shown in the remaining Figures.

A variety of methods, mechanisms, and/or structures may be used to provide a stiffness-matched structure. As one example, the stiffness-matched structure may be provided by a material configuration as disclosed in U.S. patent application Ser. No. 15/372,290. As another example, the stiffness-matched structure may be provided by topology-optimized structures. As a further example, the stiffness-matched structure may be provided by special materials (e.g., foamed metal or polymer, etc.).

A variety of methods, mechanisms, and/or structures may be used to provide a load-distributing structure. For example, the structure disclosed in U.S. patent application Ser. No. 15/372,290 is load distributing because load is carried through the structure rather than being directed to a frame or main structure. The Bed-Of-Nails design is load distributing inasmuch as the locking plate does not shunt load to a few preferred locations on the opposite side of the implant. The border frame design collects load to the outer frame, but with modification of the interfacing teeth, could operate with some load distributing capability. Other structures are possible and are still being designed.

Figure 11:
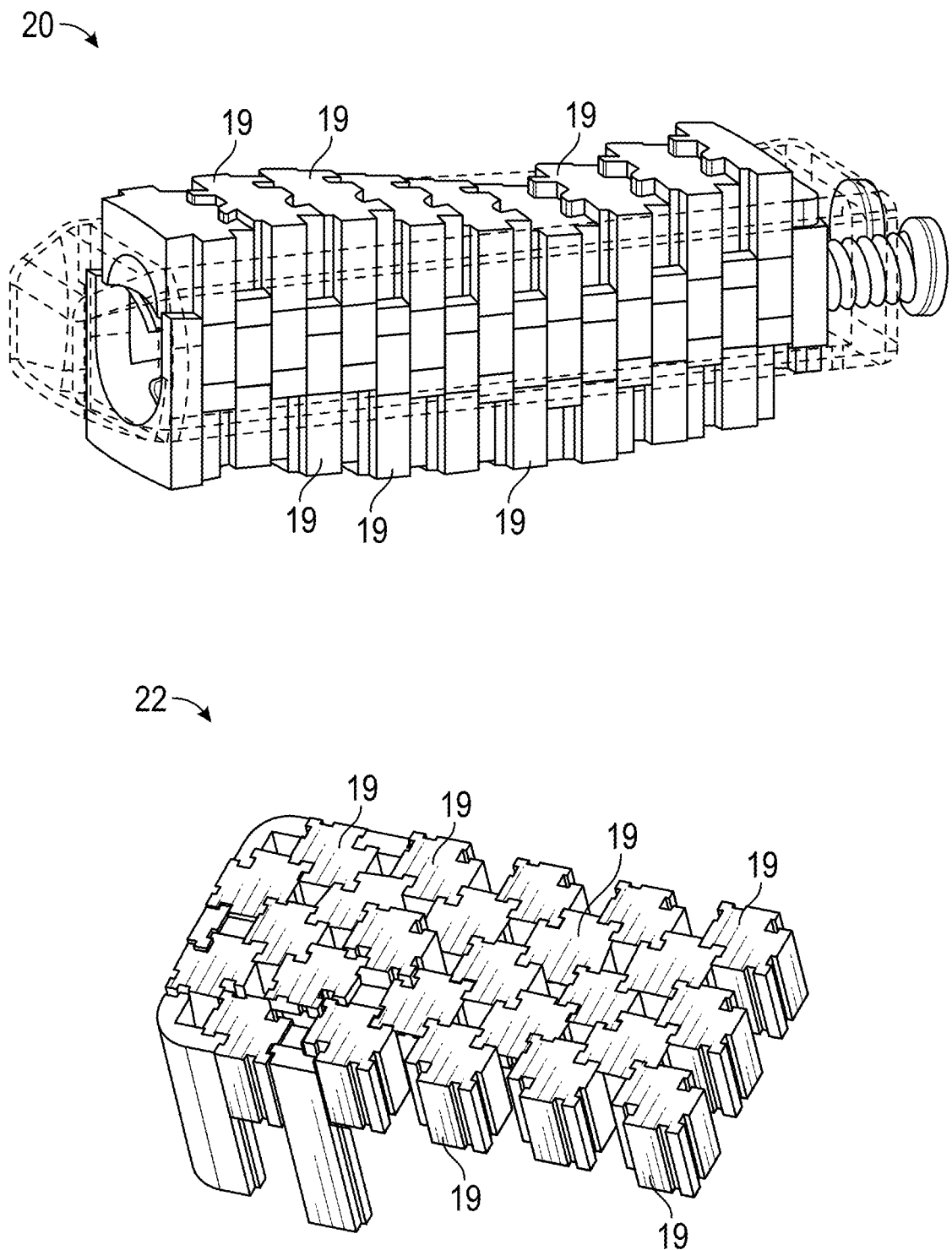
FIG. 11 shows views of an embodiment of an expandable interbody spacer.

Embodiments of the spacer that have correct stiffness (stiffness at or approaching the stiffness of cortical bone or even cancellous bone) and an ability to conform to vertebral endplate shape will minimize subsidence, endplate fracture, and stress shielding. Additionally, embodiments of the spacer that have an expansion capability reduce the carrying/inventory cost by reducing the number of heights that need to be offered/stocked. The expandability also reduces need for surgeon trialing, where the surgeon tries differently sized implants to find the best sized implant.

Where previous expanding implants were limited to having at most only one or two moving elements, allowing for at best two points of adjustment (height and lordosis), embodiments of the spacer provide multiple height-independent segments 19 forming a substantially contiguous endplate surface formed as a plurality of discrete and separate surface-forming elements, with each segment 19 serving as one of the surface-forming elements, to conform to an endplate shape, as illustrated by the views of representative embodiments of an expandable interbody spacer 20, 22 (or portions thereof) shown in FIG. 11.

Additionally, previous expanding interbody spacers often use the same mechanical feature for lifting, holding, and carrying the patient load. This might be a ramp/wedge, or the like, but it tends to collect the load to a very small portion of the implant, requiring it to be extremely strong (and stiff, unfortunately), leading to subsidence and stress shielding. In contrast, embodiments of the expandable interbody spacer as shown herein typically separate the conforming mechanism from the shape-locking/height-locking mechanism. This reduces the stiffness of the biological load path.

Figure 12:
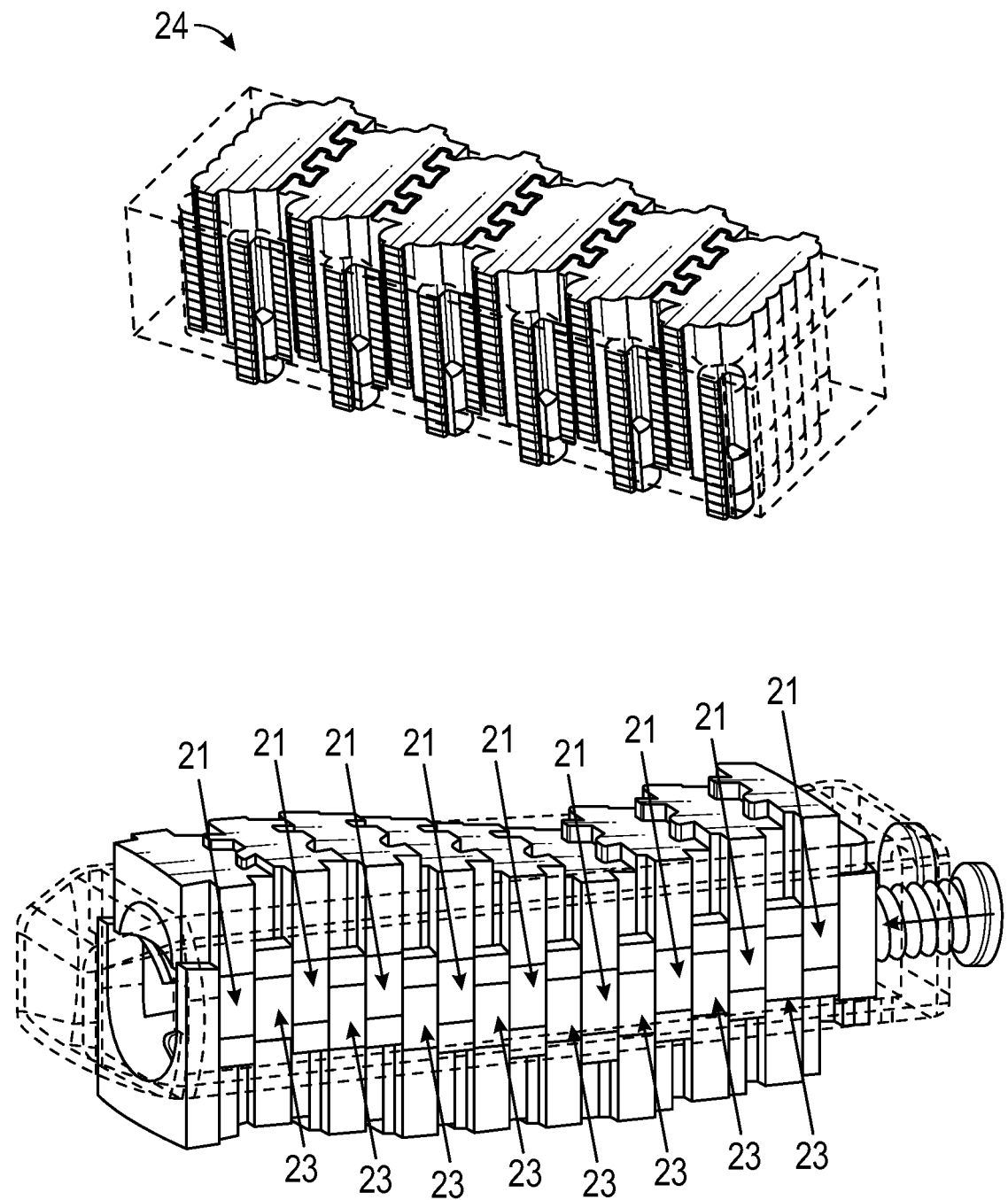
FIG. 12 shows views of an embodiment of an expandable interbody spacer.

By way of example, an embodiment of an expandable interbody spacer 24 is shown at the top of FIG. 12. In this embodiment, segments are lifted into conformance to the vertebrae by an inflatable bladder structure in center of implant. Segments then slide forward in the frame to engage teeth (1) on sides of the segments with teeth in the frame to provide multiple less-rigid load paths. AS another example, in the spacer 20 shown at the bottom of FIG. 12, each segment has a "strut" (upper arrows 021) along each side, which interdigitates the struts of the adjacent segments on the other side of the implant (lower arrows 023). By applying a light clamping force (side arrow) through the stack of struts, the conformed shape is locked and load is transmitted locally from endplate to endplate, rather than being collected into a rigid structure.

Figure 13:
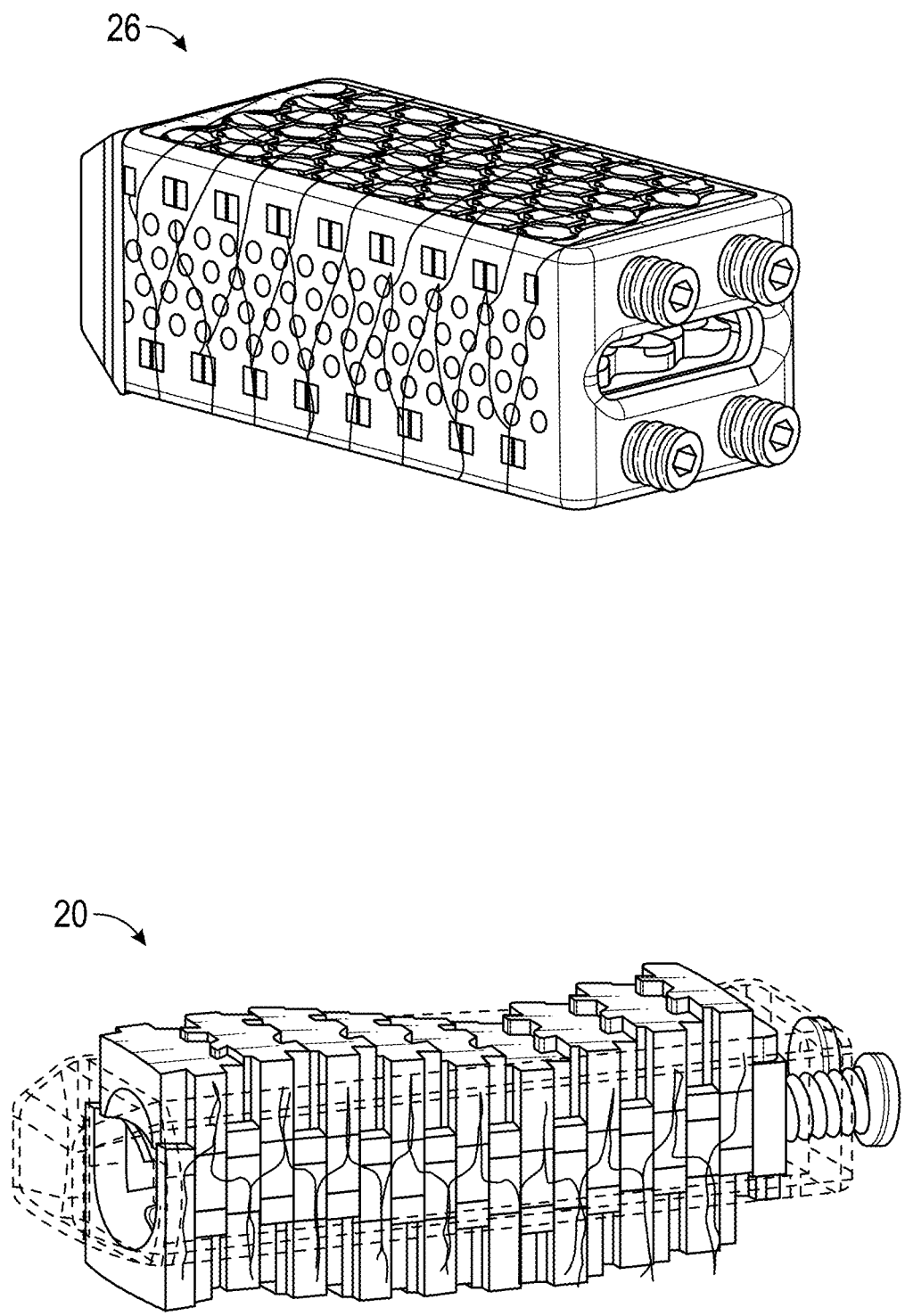
FIG. 13 illustrates how an embodiment of an expandable interbody spacer can provide stress shielding through multiple load paths.

In embodiments of the spacer, stress shielding is reduced by transmitting forces through as many paths as possible within the implant, rather than collecting forces to a rigid frame structure. FIG. 13 shows the spacer 20 as well as another embodiment of an expandable interbody spacer 26, where force lines have been drawn showing how force is distributed throughout each of the implants. These force lines extend from one side of the implant to the other, thereby passing distributed loads from one vertebrae to the next without force being too localized.

According to embodiments of the spacer, segments of the endplates that form a contacting surface can interlock in a slideable manner to better support each other against shear, torsion, and buckling loads while still allowing sufficient relative translation to permit conforming to the vertebral endplates. Various mechanisms to do so are illustrated in FIG. 14. At the upper left, adjacent segments are joined to different elements of a nested coil, allowing a measure of relative translation but preventing lateral separation. At upper right, adjacent segments are joined by pin-slot features. In the middle, adjacent segments are connected with a grid of torsion bars which also help balance the load across the implant surface. At bottom left, adjacent small-diameter coils are linked by larger-diameter coils. At bottom right, adjacent segments are joined by compliant flexures.

FIG. 15 illustrates additional mechanisms for joining adjacent segments with a measure of flexibility. At upper left, an implant surface can be made similar to chain mail. At upper right, segments can be formed with interlocked bars. At middle left, segments may have articulating joints. At middle right, segments can have dovetail joints. At bottom left, segments themselves can be formed in interlocking shapes. At bottom right, segments can be formed with T-slots.

Figure 16:
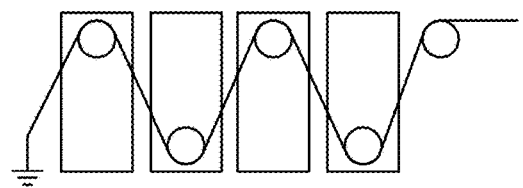
FIG. 16 illustrates mechanisms for distributing lifting of embodiments of an expandable interbody spacer to achieve conformance to the vertebral endplates.
Figure 16:
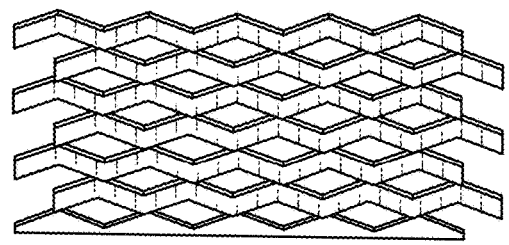
Figure 16:
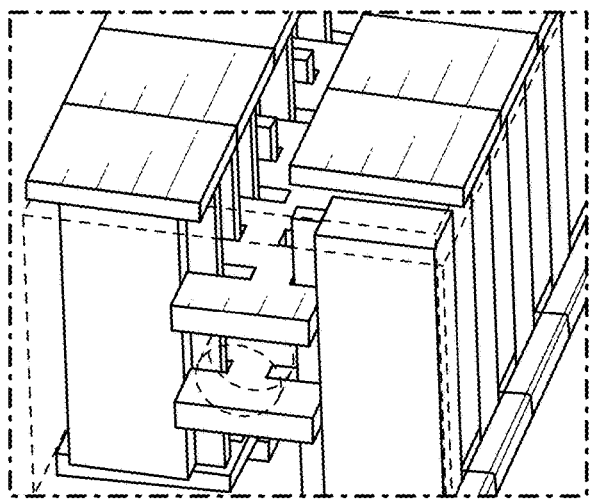
Figure 16:
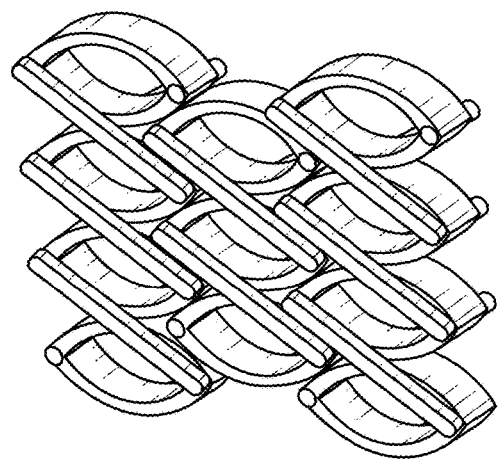
Figure 16:
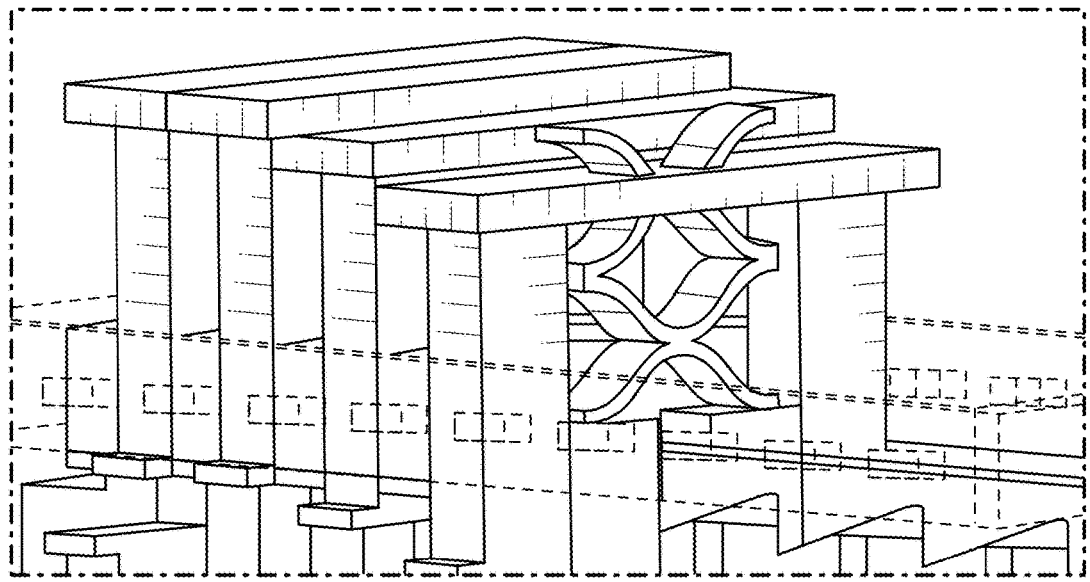

Existing expandable interbody devices also cannot conform effectively because they typically have a single lift mechanism (e.g., a ramp, a wedge, etc.). In contrast, spacers in accordance with embodiments of the invention use multiple points of lift to achieve conformance. Ideally, all points lift with equal force or bone contact pressure, unless differential lifting is desired to correct spinal posture. In many embodiments, a balloon or bladder (similar to a kyphoplasty balloon) is used as a lift mechanism, though FIG. 16 illustrates alternate embodiments. At upper left, a nitonol wire with constant tension, acts on pulleys on opposite-facing segments and can lift with equal force per segment. At upper right, building up the implant from corrugated layers allows each layer to conform by being "springy" and allows a collapsed height (when corrugations nest) or a lifted height, when alternating layers are offset.

At the middle left of FIG. 16, a central plate has slits which pinch on rails on each segment. At the plates are lifted, the segments rise. When the force on any segment exceeds the friction generable by the pinch force, that segment stops traveling. Thus other segments continue travel until a conformed shape and distributed load have been created. At the middle right of FIG. 16, each segment can have its own spring to lift it into contact with the bone. At the bottom of FIG. 16, stacks of diamond or almond shaped springs when forced into each other laterally will expand vertically. A single force applied to the end of the stack causes all stacks to want to expand and lift.

Figure 17:
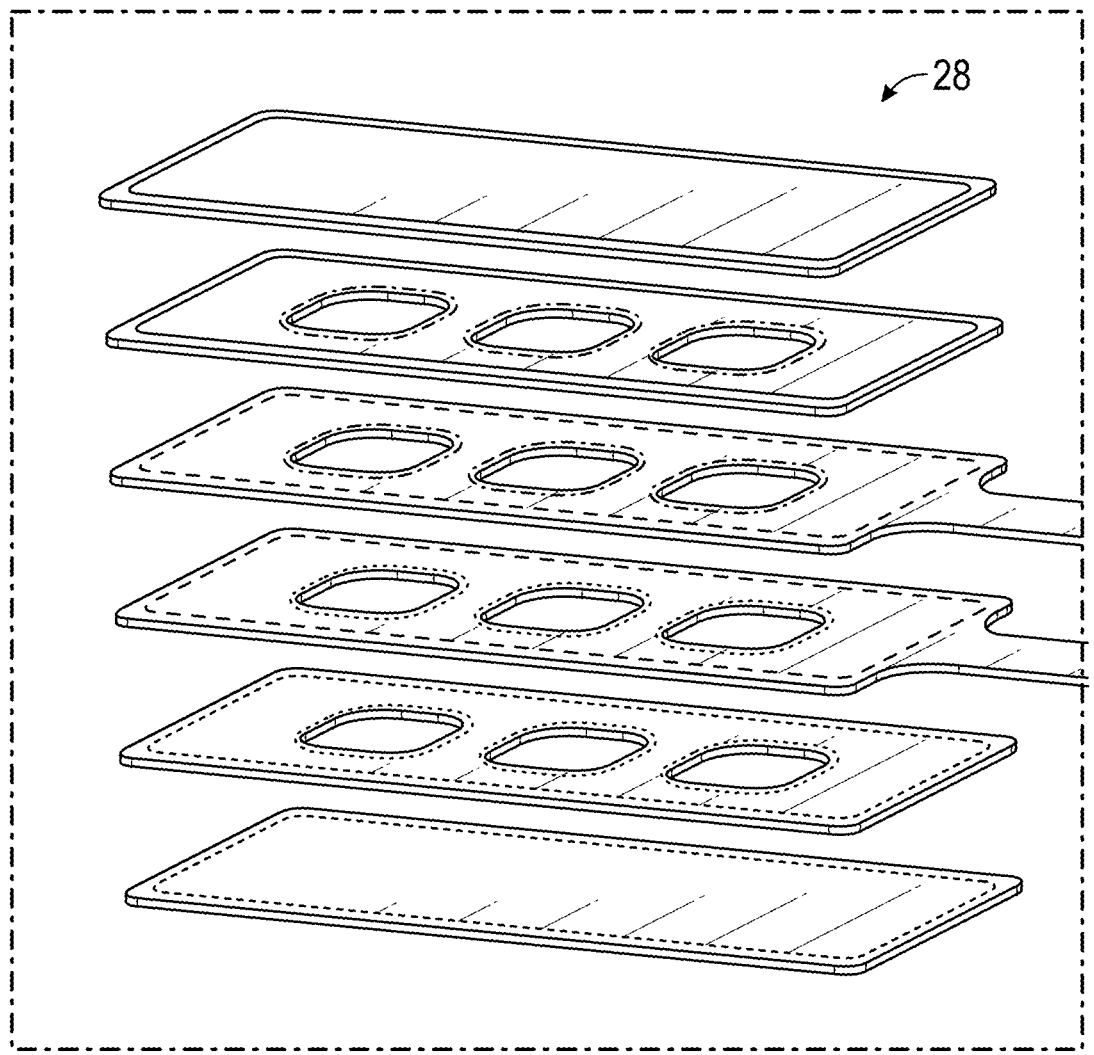
FIG. 17 illustrates an embodiment of a shape-controlled bladder for use in embodiments of an expandable interbody spacer.

FIG. 17 illustrates construction of a shape-controlled bladder 28 for use with embodiments of the spacer. Kyphoplasty balloons tend to expand equally in all directions, but for an expanding interbody spacer, it is more desirable to have the balloon self-contain laterally (so as to not push on the walls of the implant), but to preferentially expand vertically. This can be achieved by adding some kind of internal reinforcement to the balloon to prevent expansion in undesired directions, or by creating a multi-layer bellows, as illustrated in the exploded view of FIG. 17, where the layers have the internal reinforcement necessary to prevent or reduce lateral expansion. This embodiment of the bladder 28 includes alternately-bonded layers to create a bellows shape that can expand vertically but is self-constrained laterally.

Figure 18:
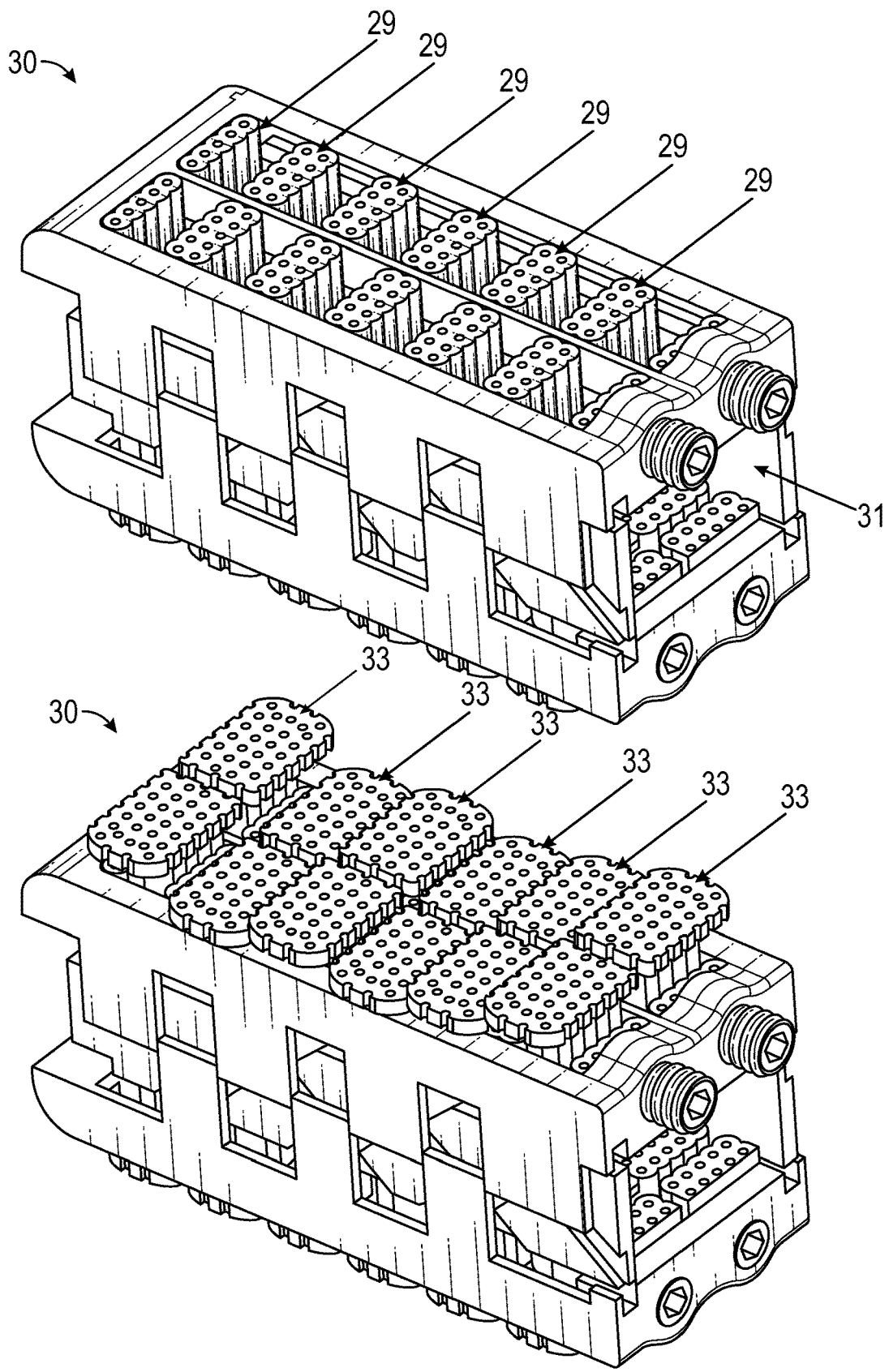
FIG. 18 shows views of an embodiment of an expandable interbody spacer.
Figure 19:
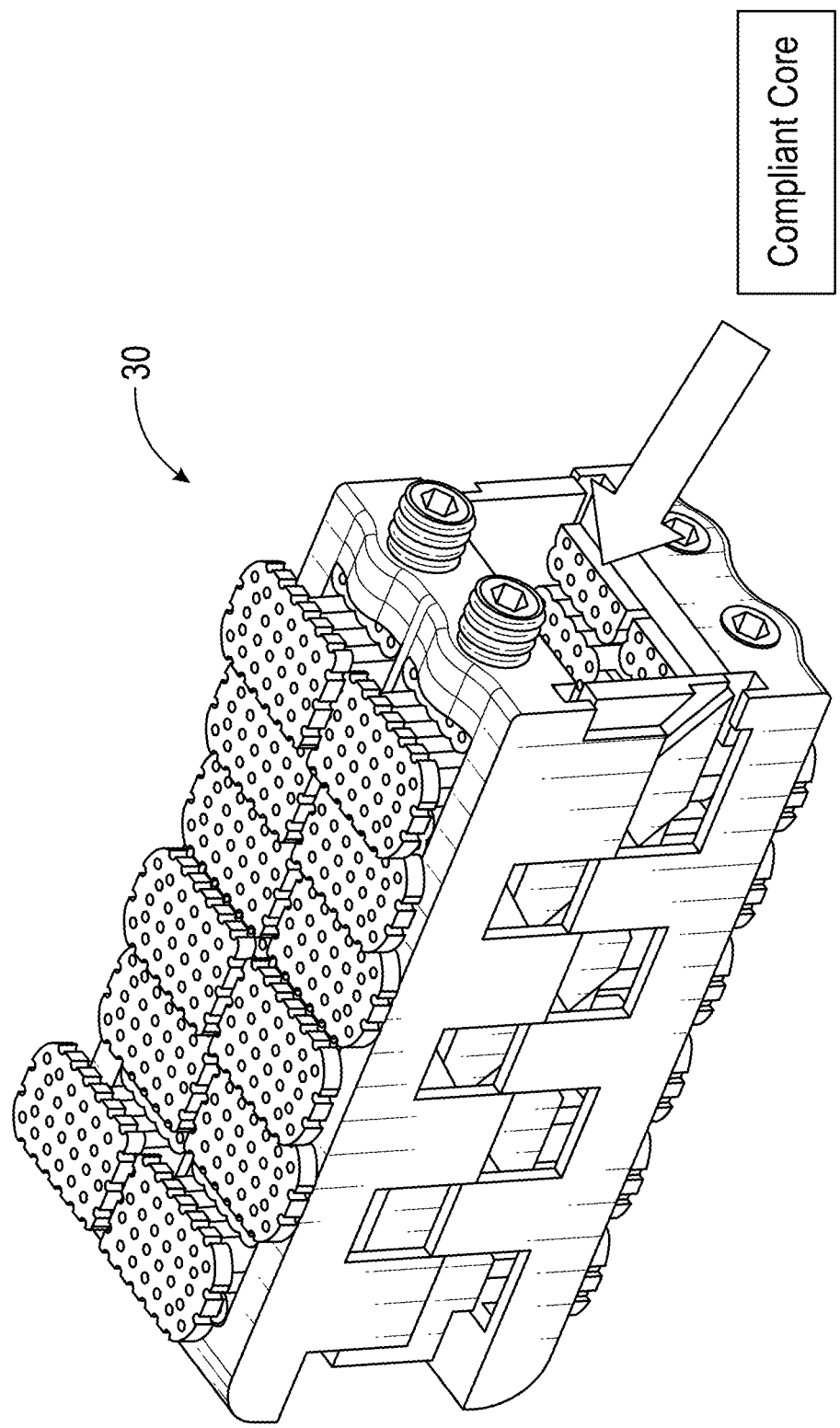
FIG. 19 shows a view of the embodiment of FIG. 18.

FIGS. 18 and 19 illustrate another embodiment of an expanding interbody spacer 30. In this embodiment, each frame half carries a set of "static" blocks (arrows 29 at the top of FIG. 18) which can slide forward and backward in the frame. Ramps on each frame half interact with ramps on "height bars" (right arrow 31 in the upper view of FIG. 18) such that height bars can separate the frame halves to increase and/or measure the "base height" of the implant. Assembly of the implant completed by adding the "moving blocks" indicated by the arrows 33 in the lower view of FIG. 18 between the static blocks. The internal balloon/bellows causes the moving blocks to conform to the endplate. It may also contribute to the force required to increase the "base height" of the implant. The end screws are tightened to compress the static and moving blocks together and lock the conformed shape. After the conformed shape is locked, the balloon/bellows is removed from the implant and replaced with a compliant core (FIG. 19). The "height bars" may be released to allow the implant to settle onto the compliant core.

Figure 20:
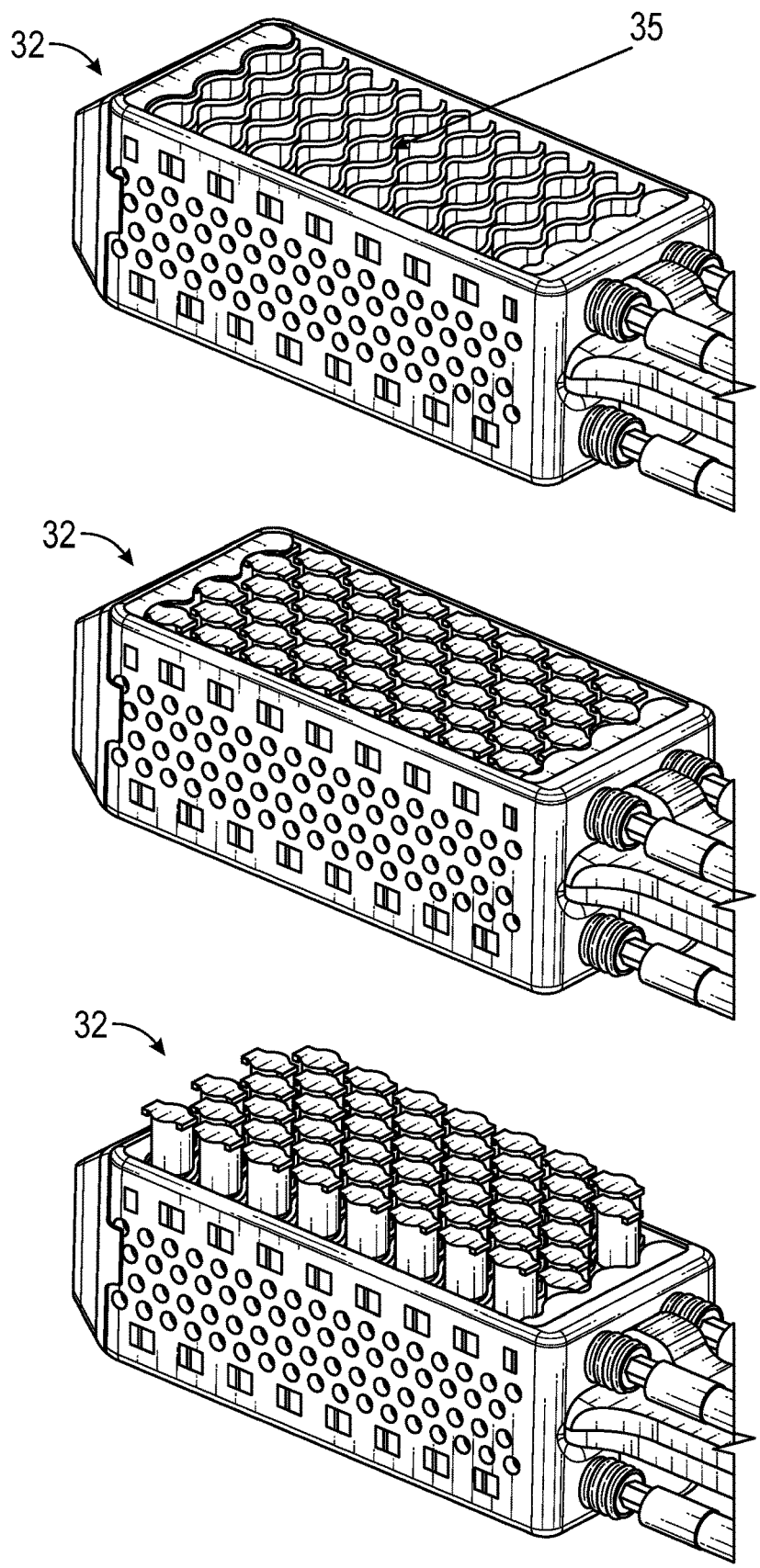
FIG. 20 shows views of an embodiment of an expandable interbody spacer.

FIG. 20 illustrates another embodiment of an expanding interbody spacer 32. In this embodiment, a compliant/porous frame is fitted with multiple cross members 35 which can translate a short distance forwards and backwards in the frame rails (upper view of FIG. 20). The assembly is completed by adding displacement-limited "pistons" between the cross members 35 (middle view of FIG. 20). The balloon/bellows is inserted between the upper and lower layer of pistons. Under balloon pressure, the pistons move outward to conform to the endplate shape and provide a distraction force (lower view of FIG. 20). Pistons on the underside of implant would also extend/conform, but are not shown in these views. The end screws (or other mechanism) compresses the cross members and pistons to frictionally lock the conformed shape and height. The inserter tool is removed and implant is post-packed with bone graft, etc. if desired.

Figure 21:
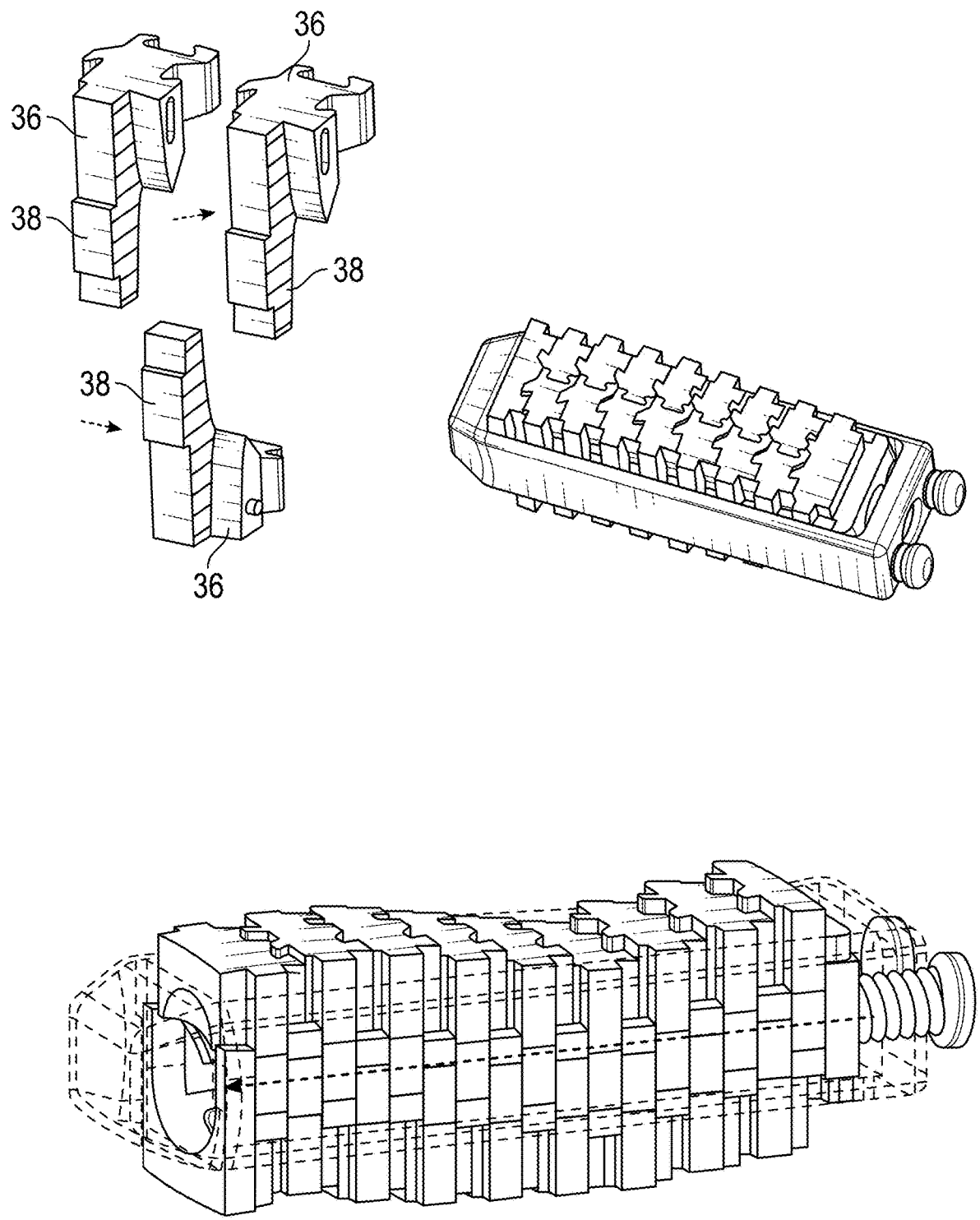
FIG. 21 shows views of an embodiment of an expandable interbody spacer.

FIG. 21 illustrates another embodiment of an expanding interbody spacer 34 (central view of FIG. 21). In this embodiment, the implant includes multiple compliant segments 36 (top view of FIG. 21) supported by fingers 38. Fingers 38 of upper segments slide on fingers 38 of lower segments on indicated surfaces. Multiple segments lock together to create a full implant as shown in the central view of FIG. 21.

Returning to the spacer 20 (lower view of FIG. 21), the bladder, balloon, or bellows gives the implant conformed shape and provides a distraction force. Screws or some other locking mechanism compresses all fingers together through the load path shown to frictionally lock them together to maintain the conformed shape and height. The bladder, balloon, or bellows may then be removed and post-packing occurs, if desired.

Figure 22:
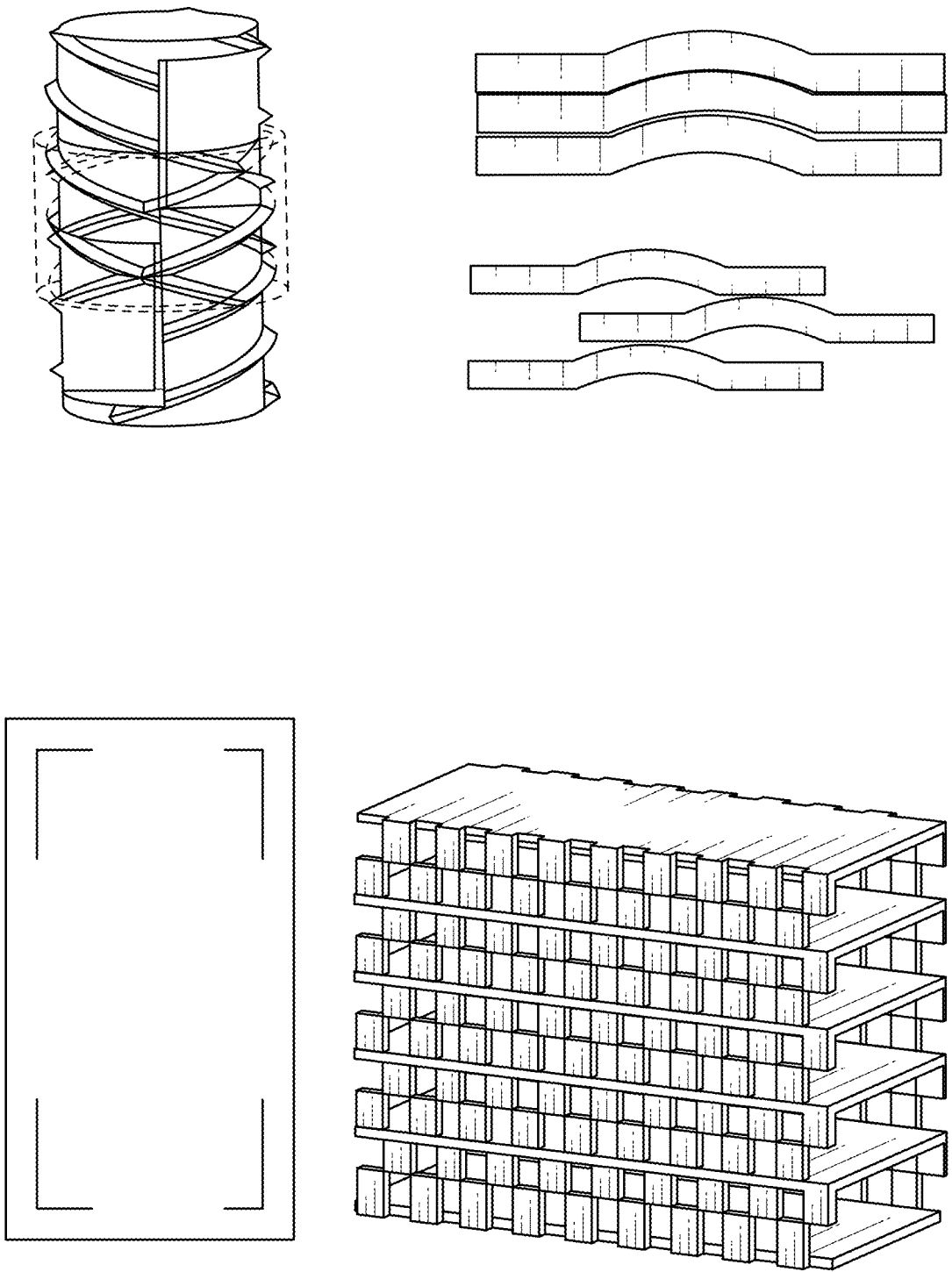
FIG. 22 illustrates alternate methods for lifting and separating portions of embodiments of an expandable interbody spacer.

FIG. 22 shows other options for providing a distraction force to the halves of the implant. In one example, instead of using a balloon as a lift mechanism, the implant is filled with something biocompatible and extremely hydrophilic such that saline is applied and it swells at a certain pressure to conform and lift. As another example, (leftmost view of FIG. 22), by controlling male/female sides, and applying interdigitate to a cylinder, you can create a mechanism which includes, simultaneously, a left hand and right hand thread and can extend and lock from a simple rotation. Multiple instances of these cylinders would create an implant. Another idea uses nested dimples on sheet-metal layers (middle left view of FIG. 22) to lift and can be extended by moving the dimples to different areas of the implant and thus providing height control of left vs right and anterior vs posterior. Static layers can be "toothed" together to preserve implant footprint across height.

Figure 23:
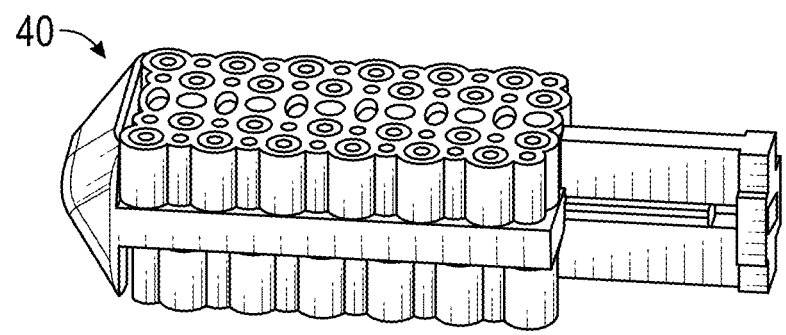
FIG. 23 shows views of an embodiment of an expandable interbody spacer.
Figure 23:
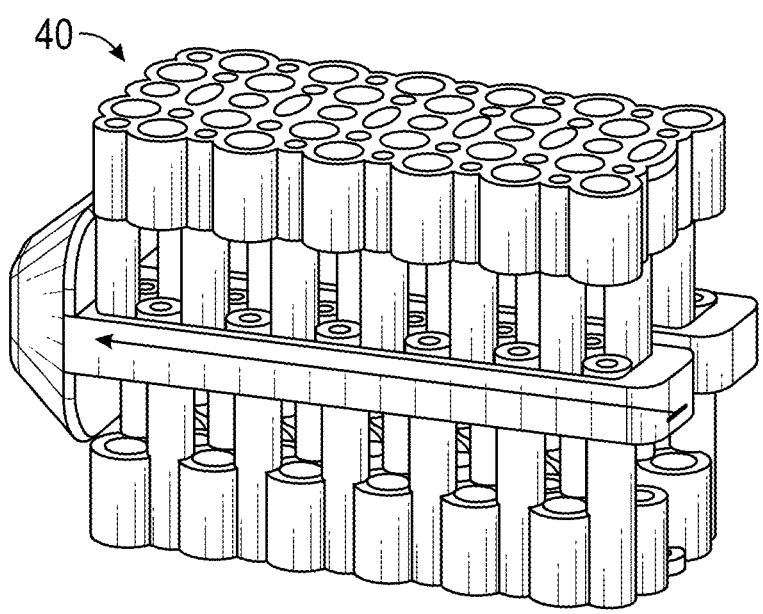
Figure 23:
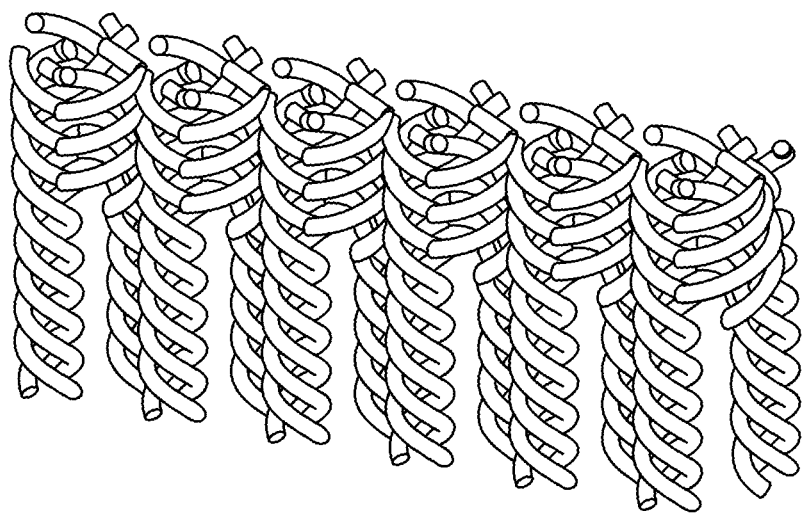
Figure 24:
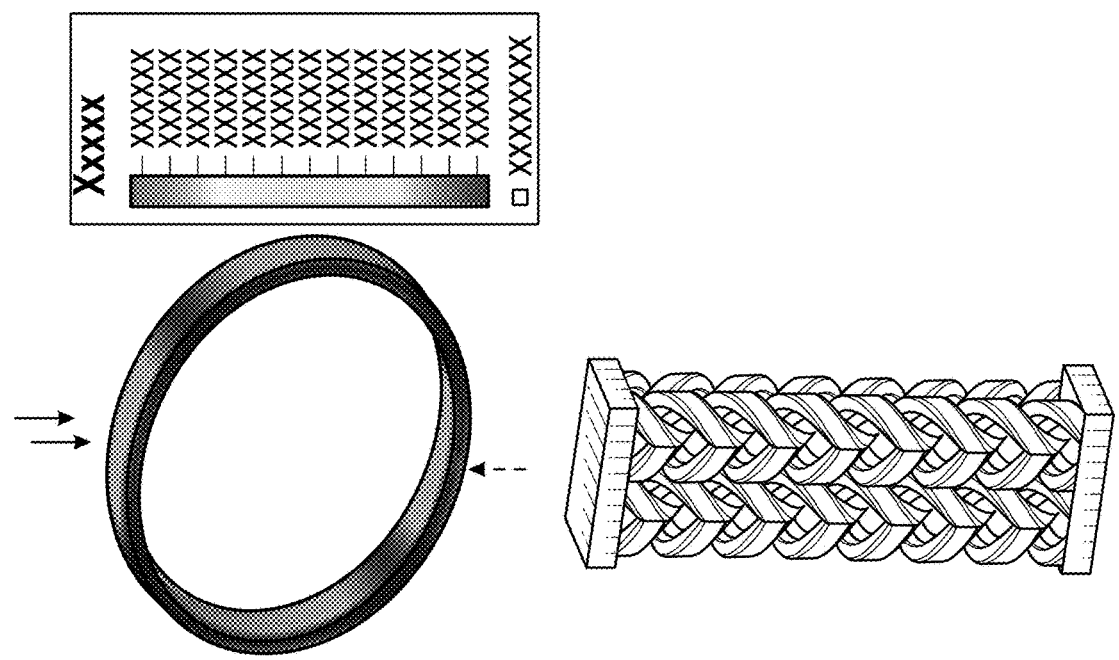
FIG. 24 shows views of alternate configurations to create a conformable surface.
Figure 24:
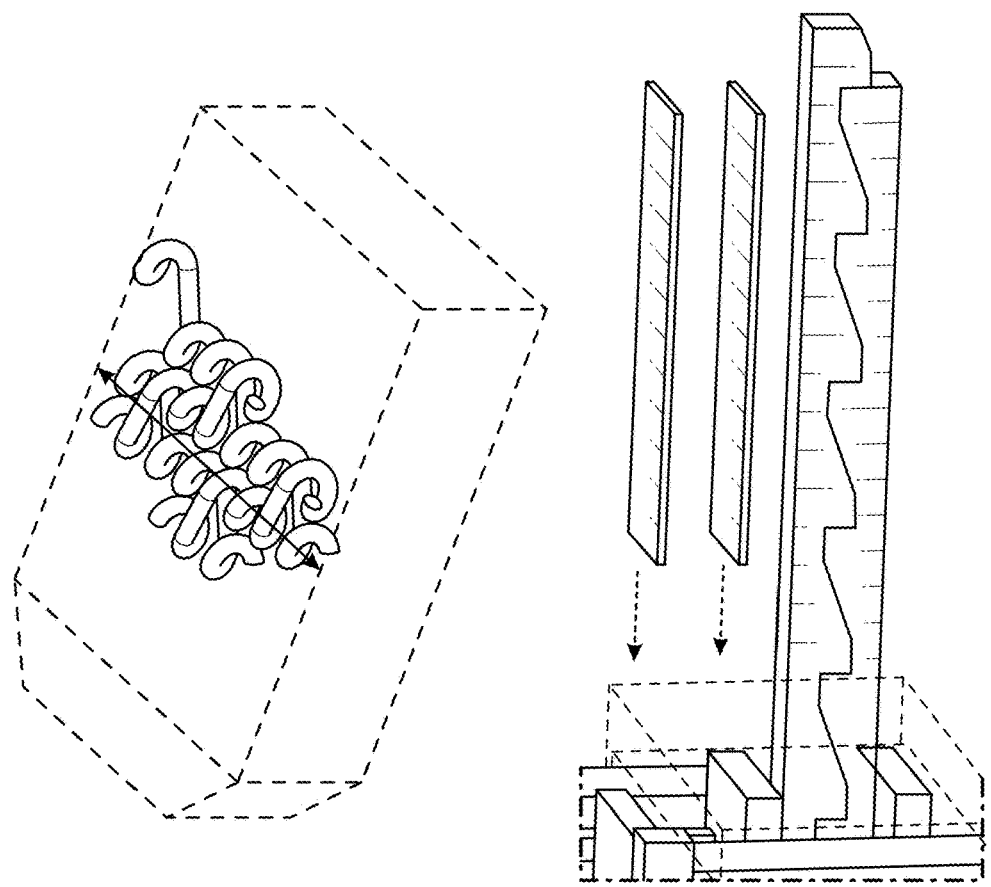

FIG. 23 illustrates another embodiment of an expandable interbody spacer 40. In this embodiment, interlocking coils are created in upper and lower sets and placed in a dual slot frame (upper view of FIG. 23). After expansion (middle view of FIG. 23), the height is locked by compressing the interdigitated small coils. Interlocking coils (lower view of FIG. 23) can be extended in their conformability by not tying the multiple leads of the same coils together. This leads to multiple, nested structures which each have their own compliance and can translate on each other.

FIGS. 24-27 illustrate other structures that can be used to provide the compliance, conformability, and other physical characteristics described previously with respect to other embodiments. In the embodiment of the upper left view of FIG. 24, a coil structure could be created laterally instead of vertically to create a conformable surface. In the embodiment of the upper right view of FIG. 24, an implant could be composed of rings tuned to the correct stiffness. In the lower left view of FIG. 24, where a ramp mechanism is used to cause height increase and/or conformance, and where space does not permit the ramp to give the implant full height in a single stroke, shims could be inserted between strokes to increase the reach of the implant. In the lower right view of FIG. 24, a concept of using blocks of compliant structure composed of smaller diameter coils than those disclosed in U.S. patent application Ser. No. 15/372,290 in order to improve spatial density and coil stability in a small space is illustrated.

Figure 25:
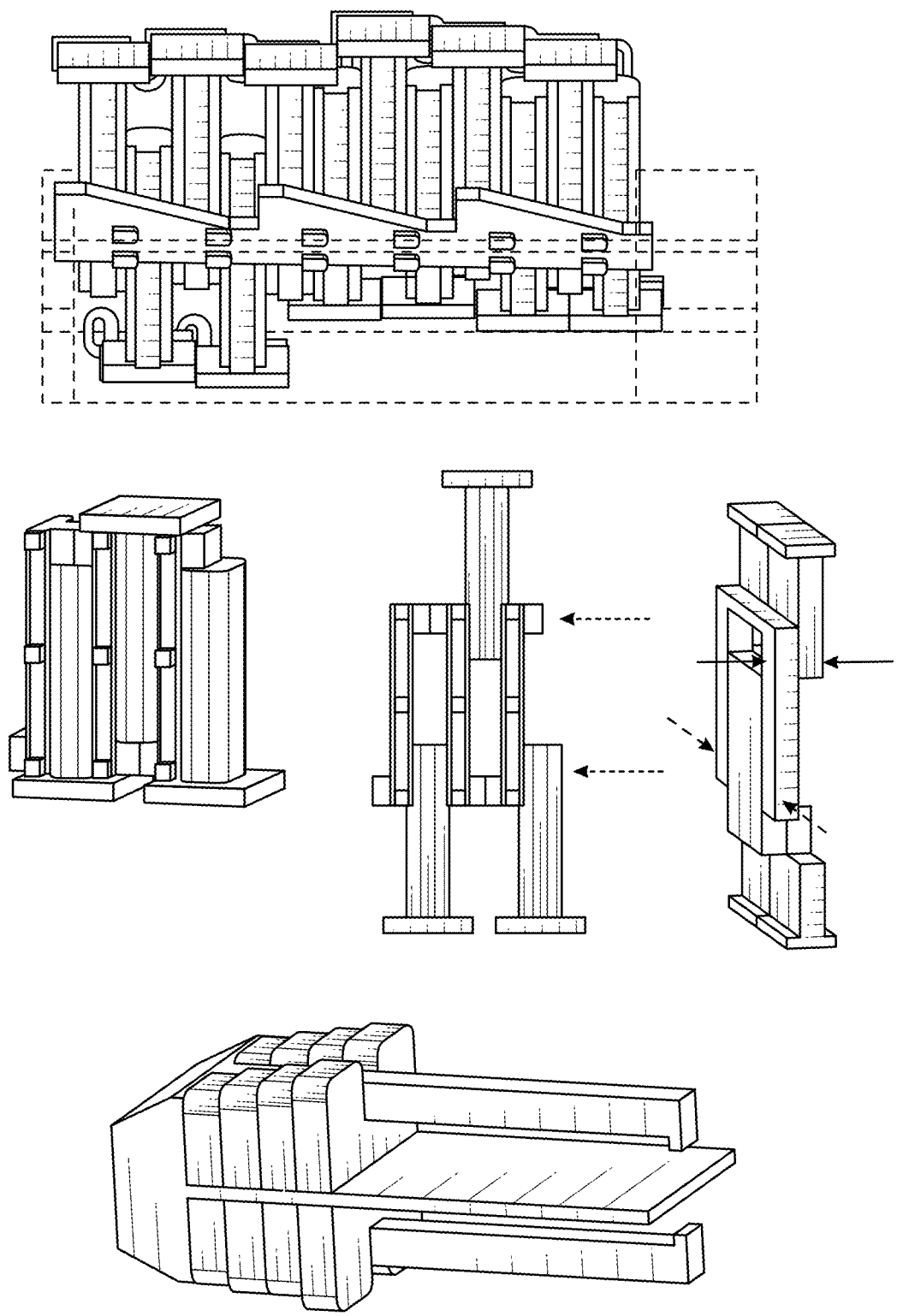
FIG. 25 shows views of alternate configurations to create a conformable surface.

In the embodiment shown in the upper view of FIG. 25, a segment stack is lightly loaded with a clamping force. A lifting mechanism incrementally lifts to a given height and then is withdrawn. Any segments with load exceeding the friction generated by the clamping force will "retreat" until other segments come into contact with the bone and the load is distributed over the segment. The clamping force is then increased to a final value to set the shape and height. Post-packing of bone graft can then occur.

In the embodiments illustrated by the middle three view of FIG. 25, the concept of interdigitation is extended with a middle layer such that the segments on each side can move out farther and still be shape-locked. There are now two clamping paths. The achievable height increase is significant. The concept of multiple clamping paths used to add height can be applied by giving each path its own direction of clamping as shown in the central right view of FIG. 25. In the embodiment illustrated in the bottom view of FIG. 25, with some kind of sliding caliper, the endplate shape can be measured and then a custom implant built out of compliant segments of the correct height. Ideally, there would be a special inserter to build this in situ and not lose the smaller-access benefits of being expandable.

Figure 26:
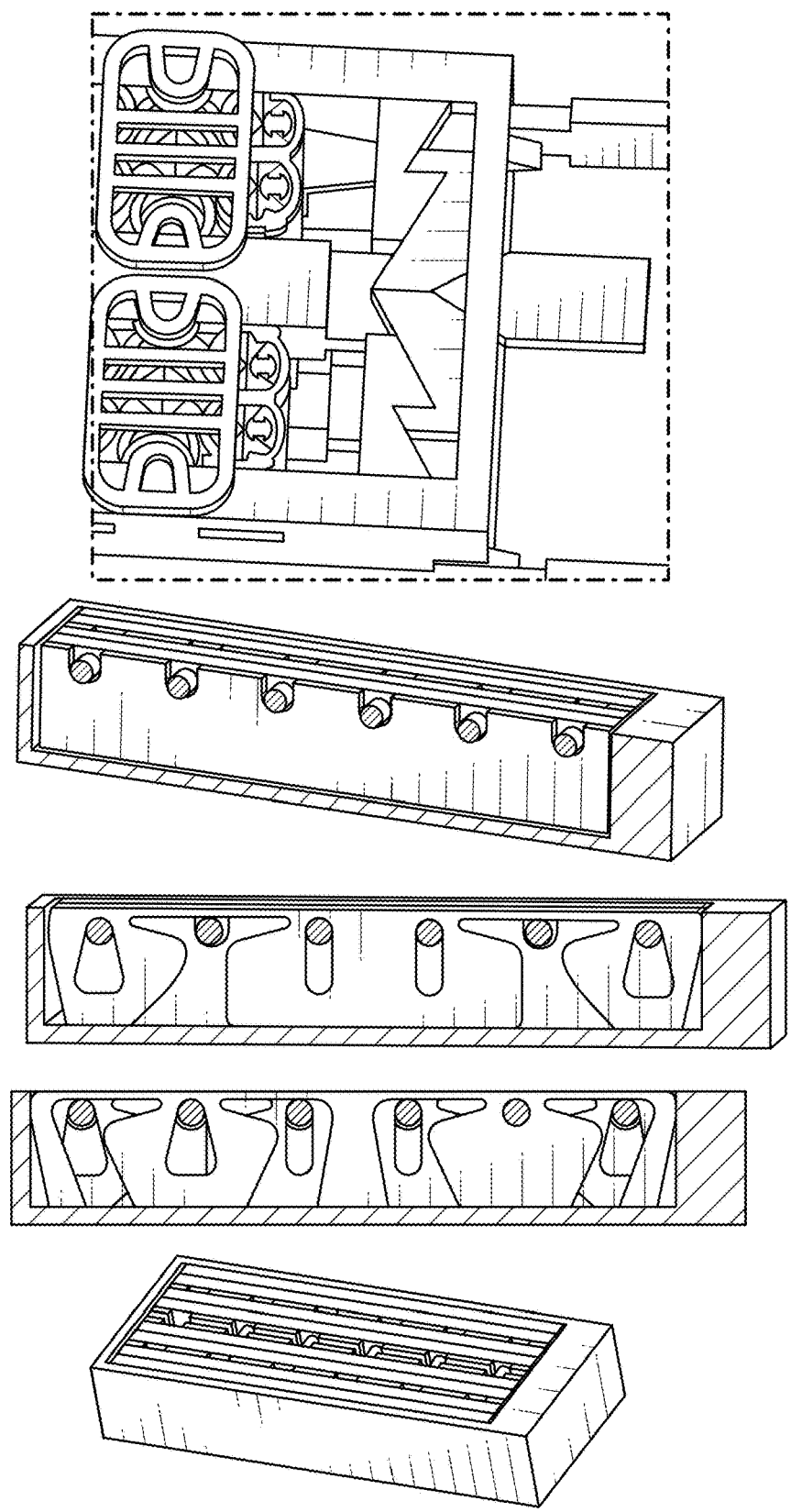
FIG. 26 shows views of alternate mechanisms to lock a conformable surface into a stable configuration.

In the embodiment of the top view of FIG. 26, as an alternative to screws, cams, ramps, and/or wedges can be used to lock stacks of blocks or fingers. In the embodiment of the lower four views of FIG. 26, an implant may be built out of multiple compliant layers that clamp against each other and against a ground layer to remember an arched, bridged, or conformed shape.

Figure 27:
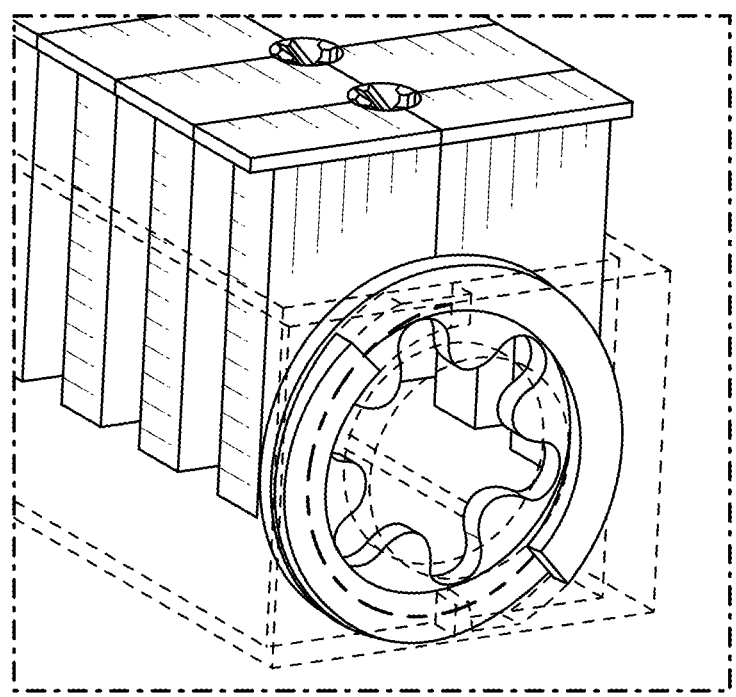
FIG. 27 shows views of alternate driving mechanisms for causing embodiments of an expandable interbody spacer to expand.
Figure 27:
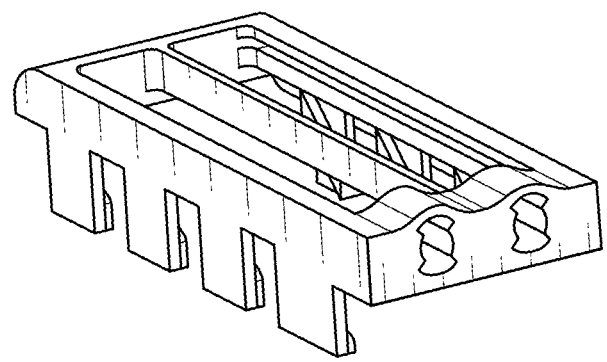
Figure 27:
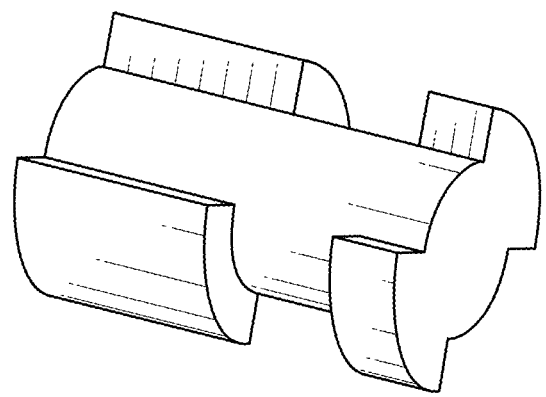

In some embodiments, as illustrated by the top view of FIG. 27, use of a face thread driver instead of a male-female thread avoids the radial space loss of the thread overlap area. This provides for a larger driver and better access for balloon and post-pack than a single male-female thread. The face thread can be left handed on one face and right handed on the other to reduce the ramp angle of the thread and thus reduce frictional losses. Multiple starts are possible to save space as well. In some embodiments, as illustrated by the lower two views of FIG. 27, conventional threaded locking mechanisms could be replaced by a quarter-turn element which always locks to the same kinematic position, saving the surgeon the trouble of worrying that the surgeon didn't tighten screws enough or that some extraneous factor caused a driver to torque-out too early.

FIGS. 28-32 illustrate aspects of another exemplary embodiment of an expanding and conforming interbody spacer 42. These figures illustrate aspects of fabrication, assembly, and implant design that may be taken into consideration. In some embodiments, the implant can be formed through an additive manufacturing process (e.g., 3D printing, sintering and the like). Clearance between parts is tuned such that the implant can print as an assembled unit without having adjacent surfaces fuse. Clearance has to be considered between conforming segment and pocket (circle marked in the lower view of FIG. 28), segment and segment (upper square marked on that view), segment and travel limiters (triangles marked on that view), cross bar and frame (two horizontal lines marked on that view), cross bar and cross bar (two vertical lines marked on that view), frame and end bar (curved line toward the right side of that view), etc. and may have different values at different locations. For improved avoidance of adjacent moving component fusing during 3D printing, the implant can be designed with an end portion of the frame being removed and the segments and cross-webs spaced out. After support removal, the end piece can be replaced and held in place either by mechanical means or by welding/bonding, as illustrated in the top view of FIG. 29.

Figure 28:
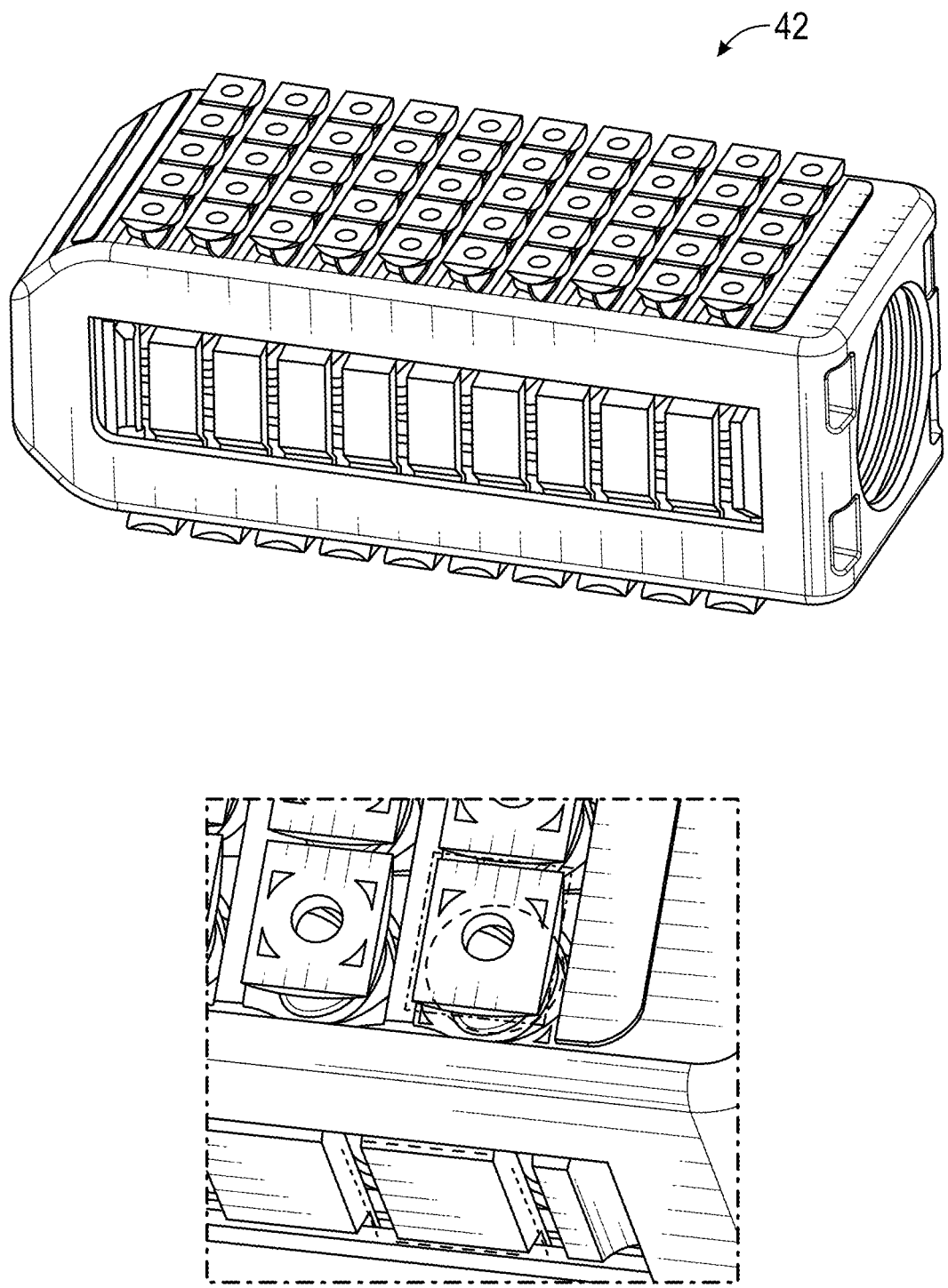
FIG. 28 shows views of an alternate embodiment of an expandable interbody spacer.
Figure 29:
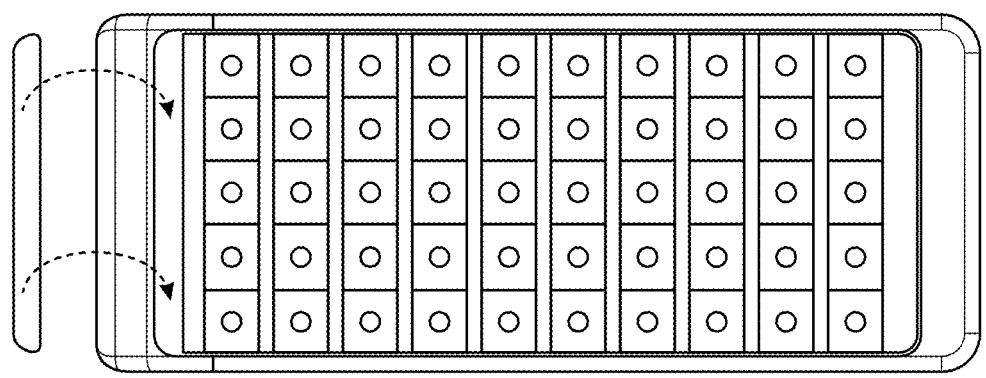
FIG. 29 shows views of the embodiment of FIG. 28.
Figure 29:
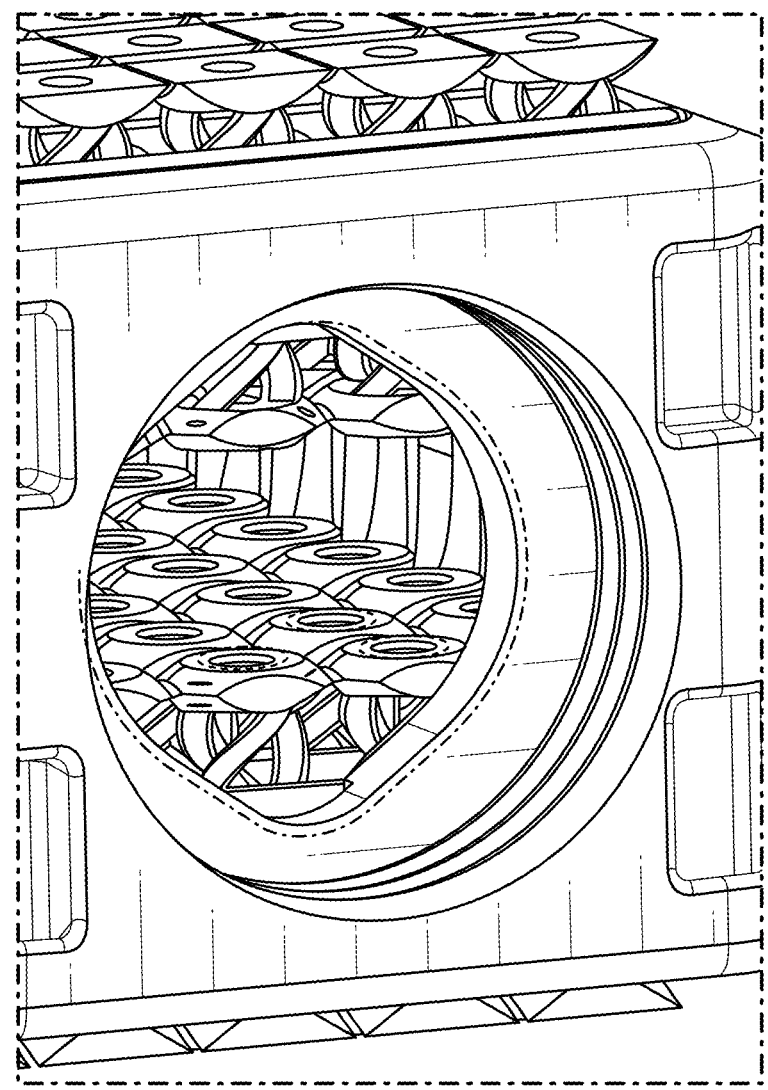

As illustrated in the bottom view of FIG. 28, the implant of this embodiment is designed with angled surfaces to facilitate self-supporting 3D printing (see the small marked lines on this view). The implant of this embodiment is also designed with droop-reducing or droop-compensating features (see the larger encompassing line on this view). Segments are designed with minimum-area horizontal surfaces to minimize the amount of support material required during 3D printing (see the smaller inner circles marked on this view.

Figure 30:
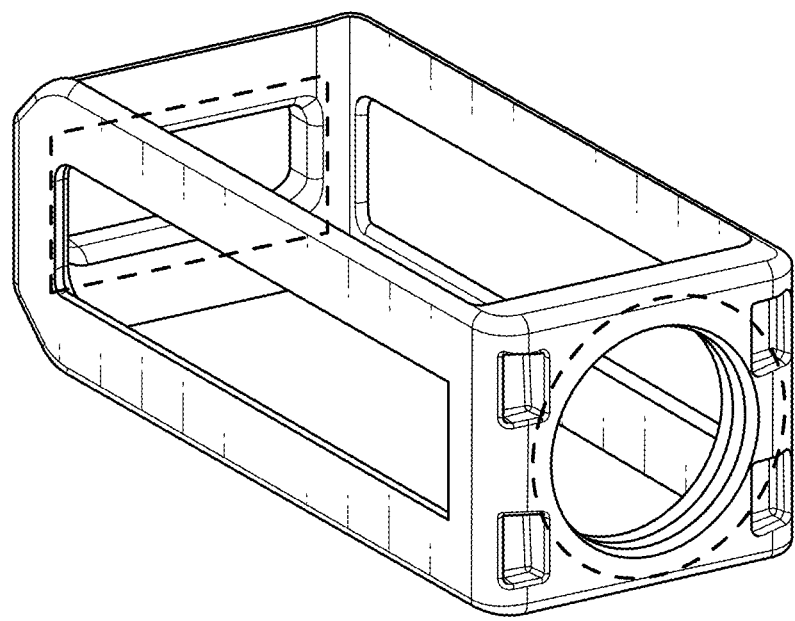
FIG. 30 shows views of portions of the embodiment of FIG. 28.
Figure 30:
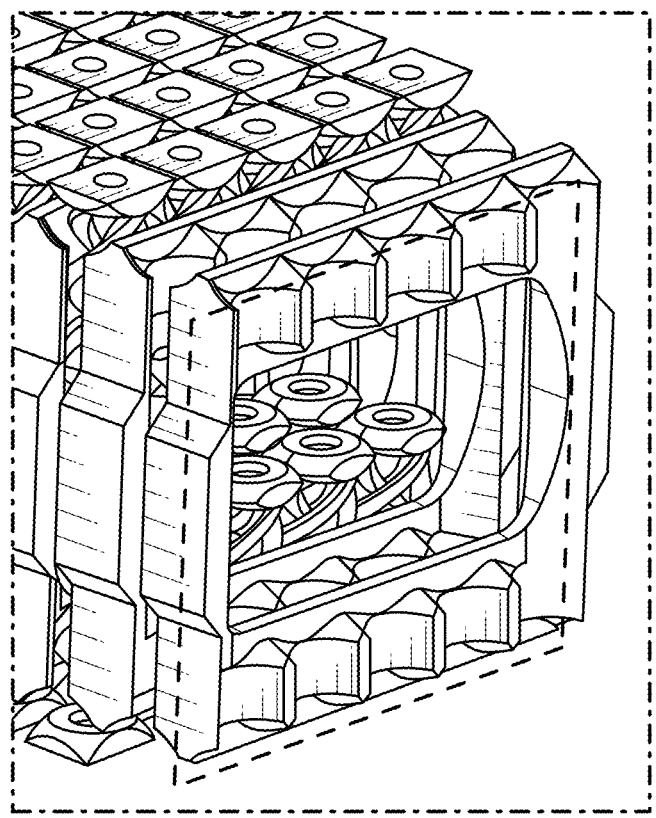

As illustrated in the top view of FIG. 30, the implant frame has openings at both ends so the inner cavity can be accessed from either side, increasing ease of support removal and making it possible to install the balloon/bellows into the inner cavity by a pull-through approach, rather than trying to push it in from one end. As illustrated in the bottom view of FIG. 30, cross-webs of this embodiment are now planar in nature instead of wavy (straight horizontal lines marked on this view). They have bosses shaped to stabilize the segments, rather than using the wave shape to stabilize segments. Wavy webs were tested and were found to be excessively compliant in the axial direction, resulting in too much stroke required of the locking mechanism. Cross-webs were joined top and bottom (vertical lines on this view) for direct load transfer rather than being separated top and bottom and sharing load through the frame. It was found that the support points on the frame (being of necessity very small) were too easy for the webs to slip off of.

Figure 31:
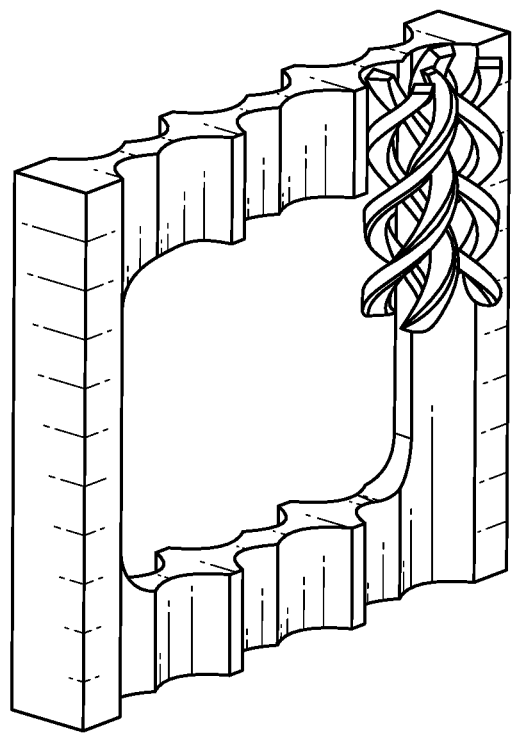
FIG. 31 shows views of portions of the embodiment of FIG. 28.
Figure 31:
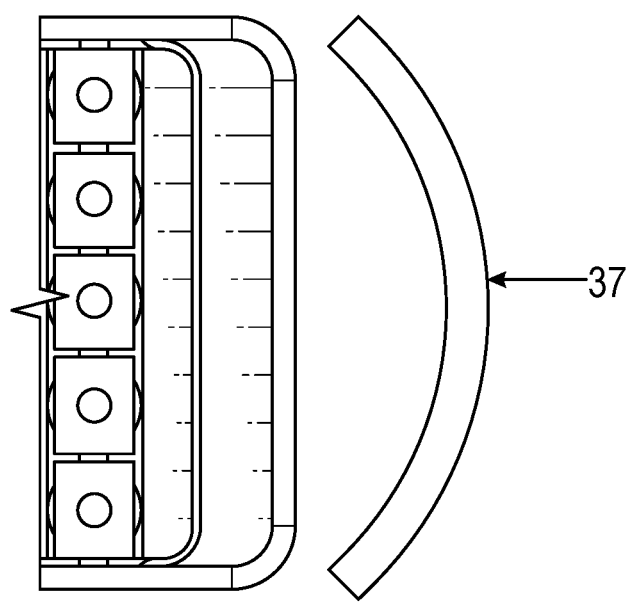

As illustrated in the top view of FIG. 31, coils can be grouped in pairs to provide rotational stability without causing excessive loss of shape-matching ability. As illustrated in the bottom view of FIG. 31, Push-Plates can be fabricated in an inverted shape (demonstrated in exaggerated form) to coming into the desired planar shape (component indicated by arrow 37) when loaded by the locking mechanism (red arrow, force) and thus distribute load evenly across the back of the segment pack. As illustrated in the top view of FIG. 32, the plate that compresses the segment stack and the frame could each be female-threaded with a slotted thread, such that they could both simultaneously engage a locking screw having both left and right hand threads. The advantage to this system is that the required axial length is reduced and the screw has positive control over the return of the compression plate, instead of relying on the spring force of the segment stack.

Figure 32:
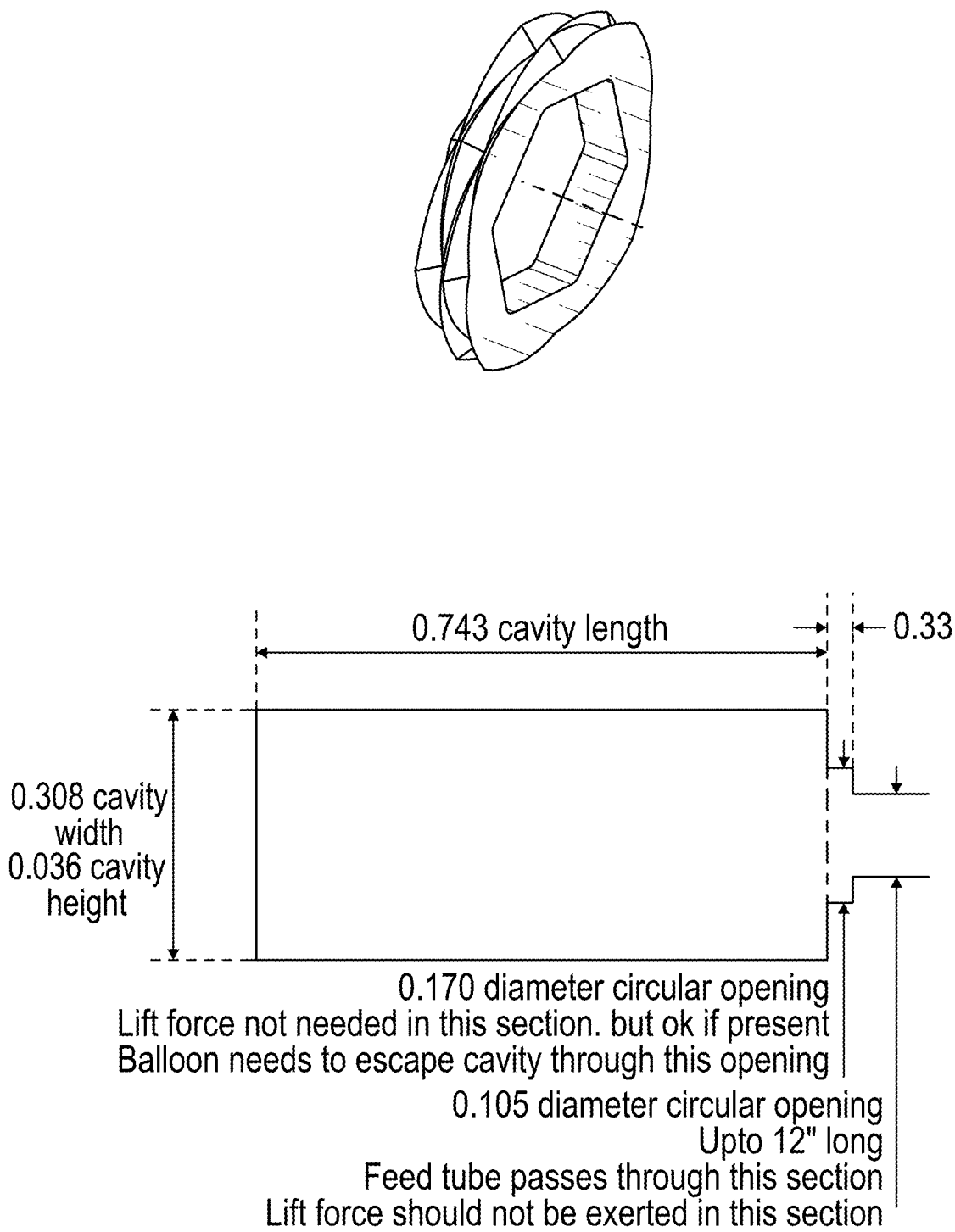
FIG. 32 shows views of portions of an embodiment of an expandable interbody spacer.

The bottom view of FIG. 32 illustrates one design of a bladder, balloon, or bellows for use with the embodiment of FIGS. 28-32. The balloon initially needs to fit in a flat, rectangular cavity. The balloon has a target strength of two cycles to 400 psi, 5 minutes each, 200 psi for 1 hour if possible. Balloon is able to escape from its cavity through an approximately 0.150" to approximately 0.170" (approximately 3.8 mm to approximately 4.3 mm) hole. The balloon ideally provides mostly a vertical lifting force, while self-limiting the lateral expansion, which puts unnecessary loads on the frame. While the diagram of FIG. 32 illustrates certain dimensions, cavity dimensions will vary based on implant footprint and height.

Figure 33:
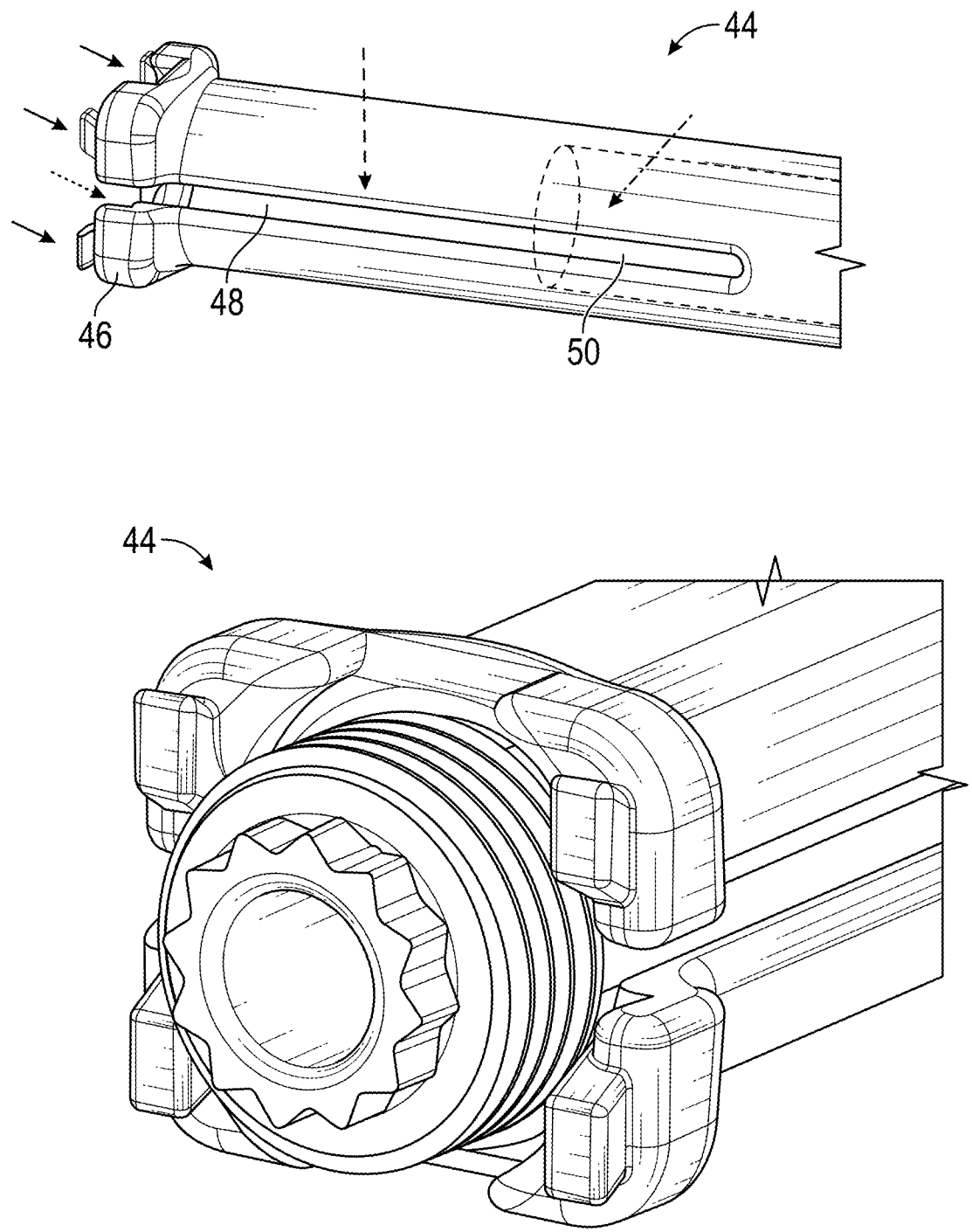
FIG. 33 shows views of an instrument for inserting and actuating embodiments of an expandable interbody spacer.
Figure 34:
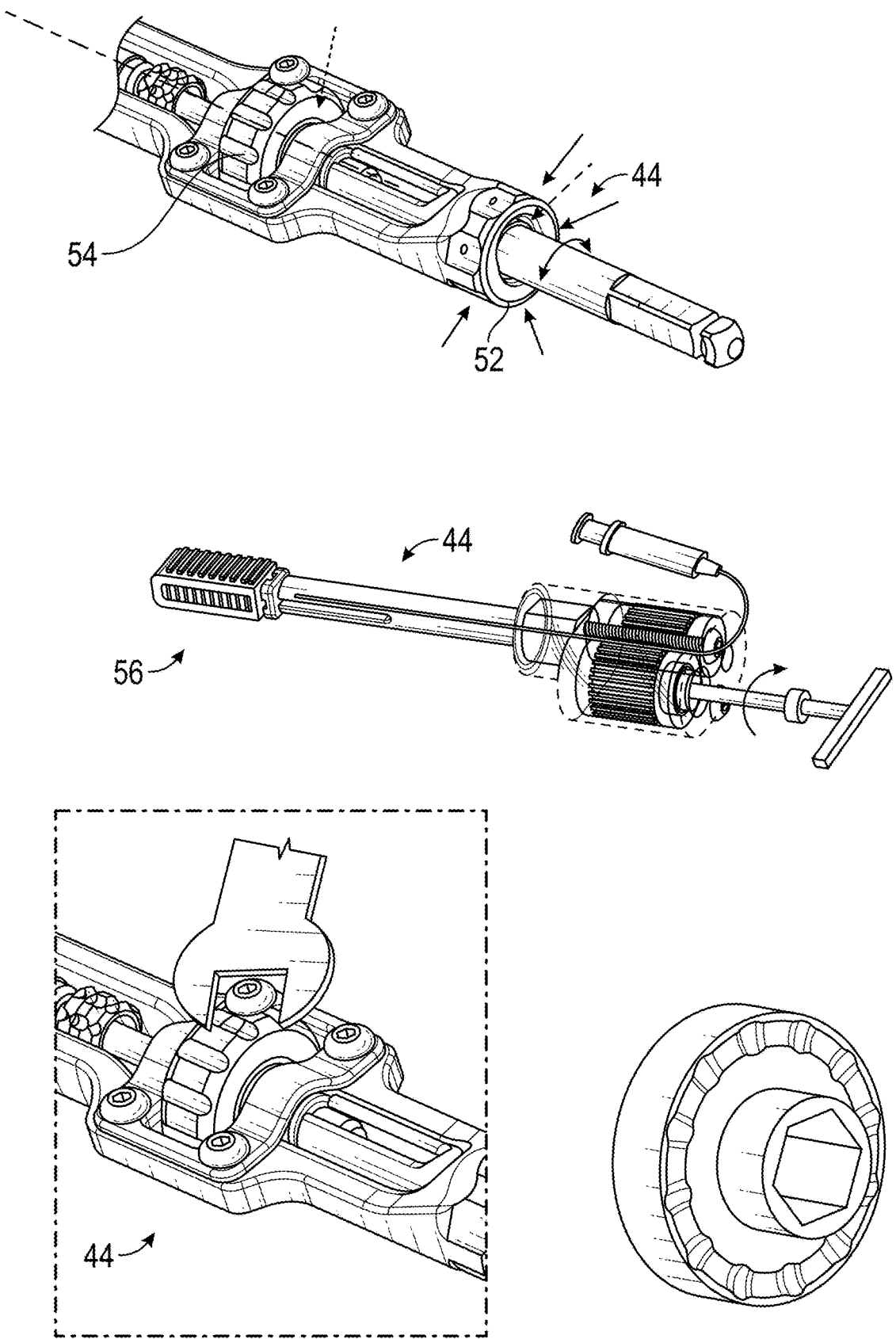
FIG. 34 shows views of instruments for inserting and actuating embodiments of an expandable interbody spacer.
Figure 35:
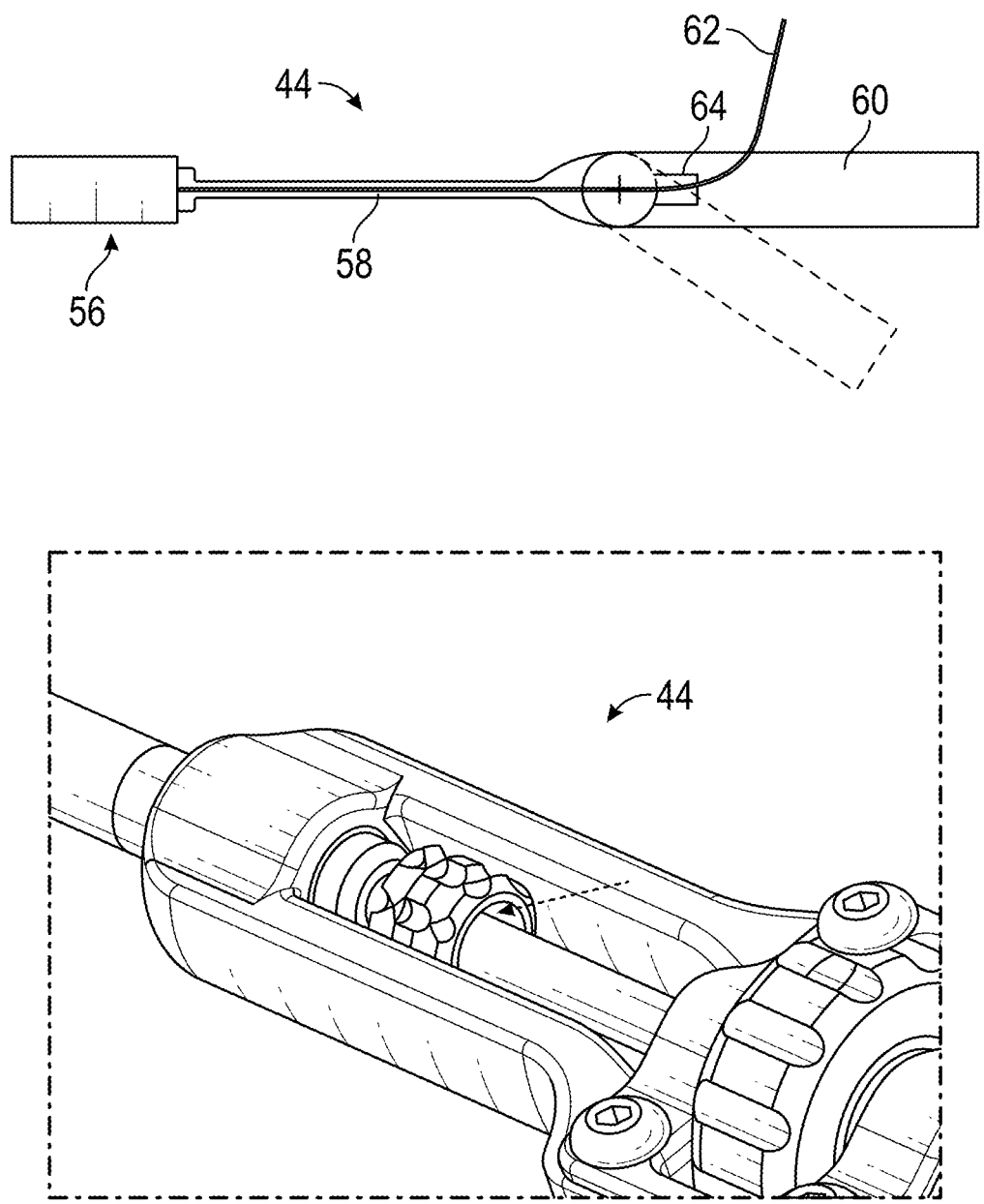
FIG. 35 shows views of instruments for inserting and actuating embodiments of an expandable interbody spacer.

FIGS. 33-35 illustrate aspects of design of an inserter instrument 44 in accordance with certain embodiments thereof. The inserter interface design has sets of opposed claws 46 (see upper view of FIG. 33) which engage pockets on the back surface of the implant, using the compliance afforded by slits 48 in the shaft of the instrument 44. When a center portion 50 of the inserter is brought forward, the claws 46 can no longer collapse inward to release the implant. The implant is thus retained until the center portion 50 is withdrawn. Because multiple items (balloon feed tube, locking driver, claw expander) have to fit through the inserter, radial space is at a premium. For this reason, driving interfaces that can transmit relatively large torques while occupying little radial space are preferred. The currently illustrated instrument/implant design uses a triple-square drive as shown in the lower view of FIG. 33. Hex, Torx, TorxPlus, or some variation thereof might also be possible, as might using a driver having castellations on the face.

Of importance is the ability to hammer on the back of the inserter instrument 44 without crushing the balloon feed tube, and to rotate the driver to activate the implant shape-locking mechanism without twisting up the balloon feed tube or depressurizing the balloon. The current instrument 44 achieves these objectives by having the top face of the inserter open such that the feed tube can exit from the driver (curved and dashed line marked on the upper view of FIG. 34) and out to the side without passing through the hammering surface at the tail end 52 of the inserter instrument 44.

The driver engages a thumb wheel 54 that allows for initial tightening of the locking mechanism by continuous rotation. For final tightening, a counter torque is attached to the tail end 52 of the instrument (at the flats) and a slotted driver is introduced-still allowing the feed tube to pass and remain under pressure. The slotted driver is limited to a small range of angular motion to prevent the tube from being sheared off. Final tightening is an incremental process.

An alternate hammer-rotate-lock solution uses a gearbox to get the rotation connection off to the side of the tube (middle view of FIG. 34). Some kind of cap for hammering on would be added to the back of the instrument. Another solution (lower left view of FIG. 34) would be to use the open-face inserter shown in the upper view of FIG. 34, but fit the thumb wheel with some kind of torque-limiting clutch, and then use some kind of wrench to rotate the thumb wheel to achieve final torque. It would be important that this clutch not overtighten the locking mechanism, but always be able to unlock it. The clutch face shown in the lower right view of FIG. 34 has different entry and exit angles to the depressions in the race, thus allowing for different release torques in the forwards and backwards directions.

The central view of FIG. 34 and the upper view of FIG. 35 shows a representative implant 56 engaged with the instrument 44. The instrument shaft 58 could have a dual-state handle 60 to protect the balloon feed tube 62 from being hammered when straight, but provide improved access to the driver 64 and feed tube 62 when rotated out of the way.

The instrument 44 can be designed such that it does not need to be detached from the implant before post-packing with bone graft etc. In this case, after the shape has been locked, the driver and balloon can be removed through the tube, the center portion 50 then expands the claws 46 on the end of the inserter instrument 44 to engage the implant 56.

Some fusion-promoting substance can then be packed into the implant through this tube, as illustrated in the lower view of FIG. 35.

Figure 36A:
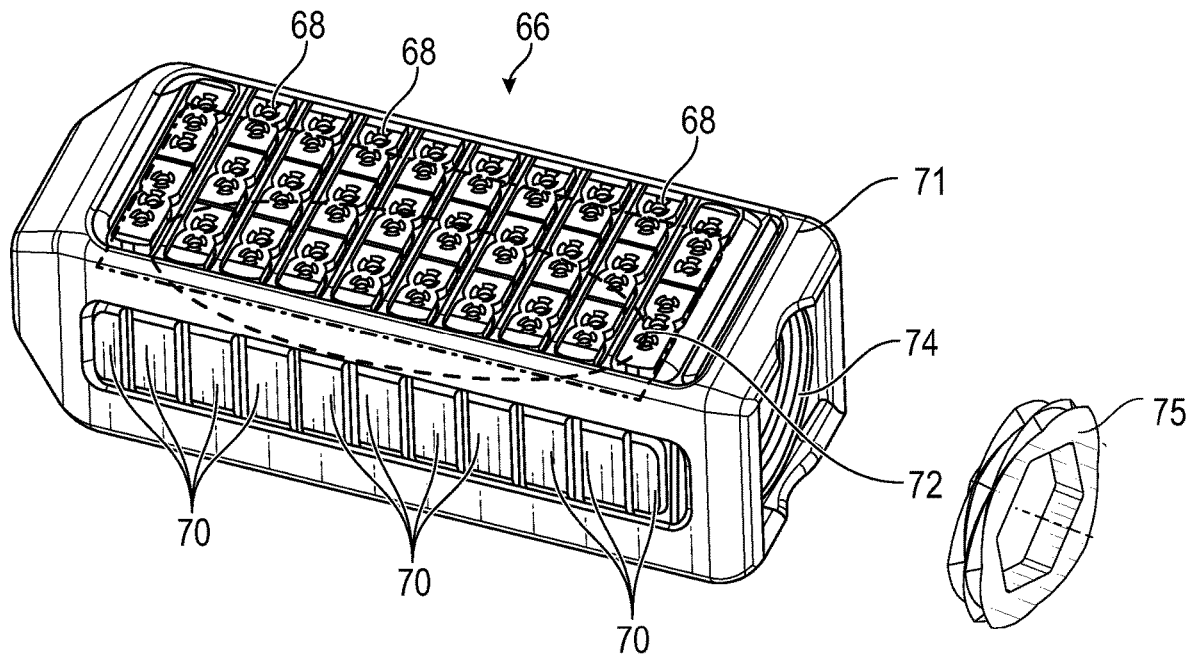
FIG. 36 shows views of an embodiment of an expandable interbody spacer.
Figure 36B:
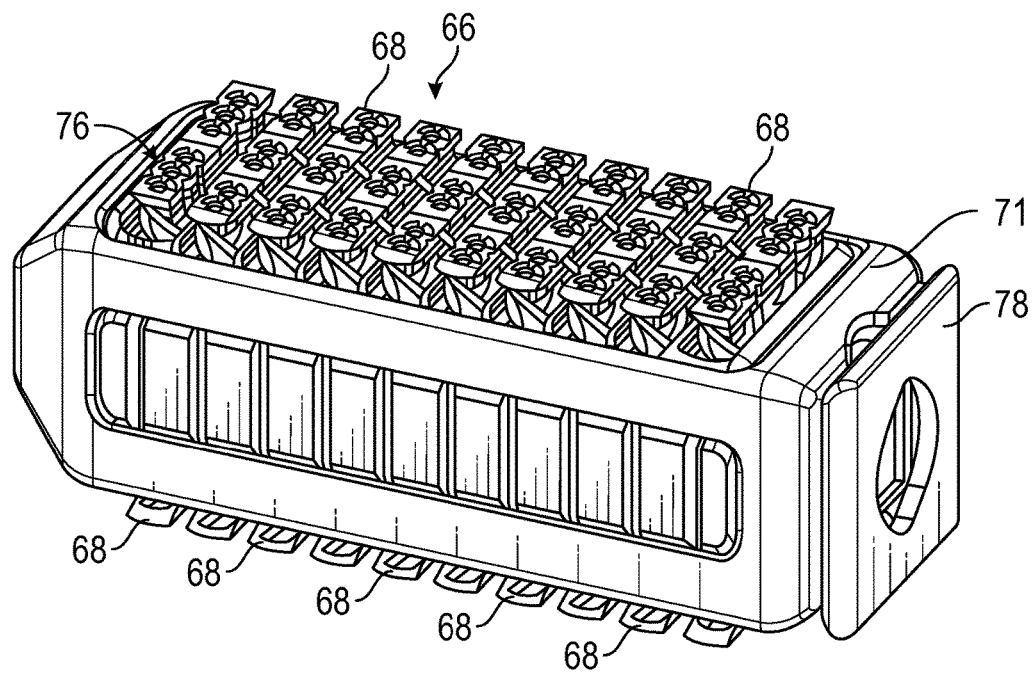
Figure 37:
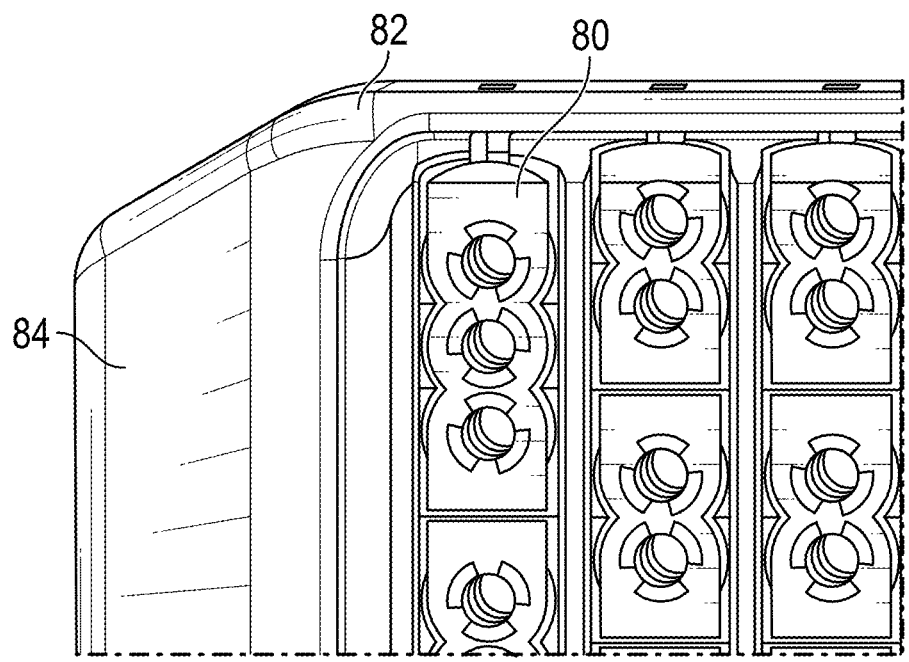
FIG. 37 shows views of portions of the expandable interbody spacer of FIG. 36.
Figure 37:
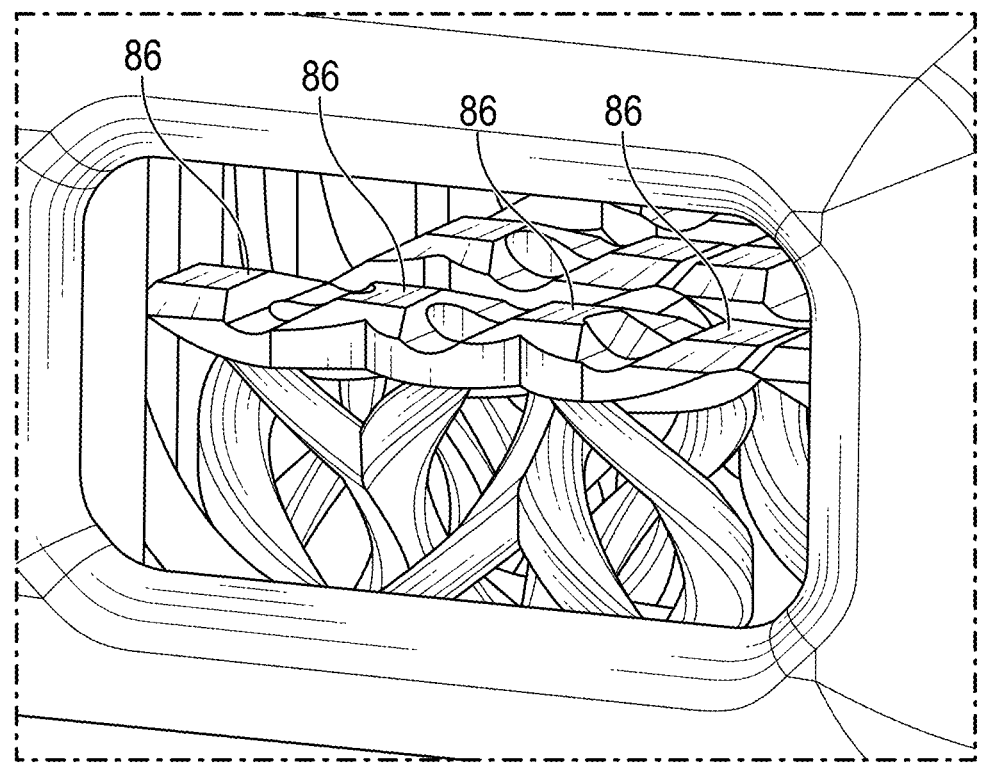
Figure 38:
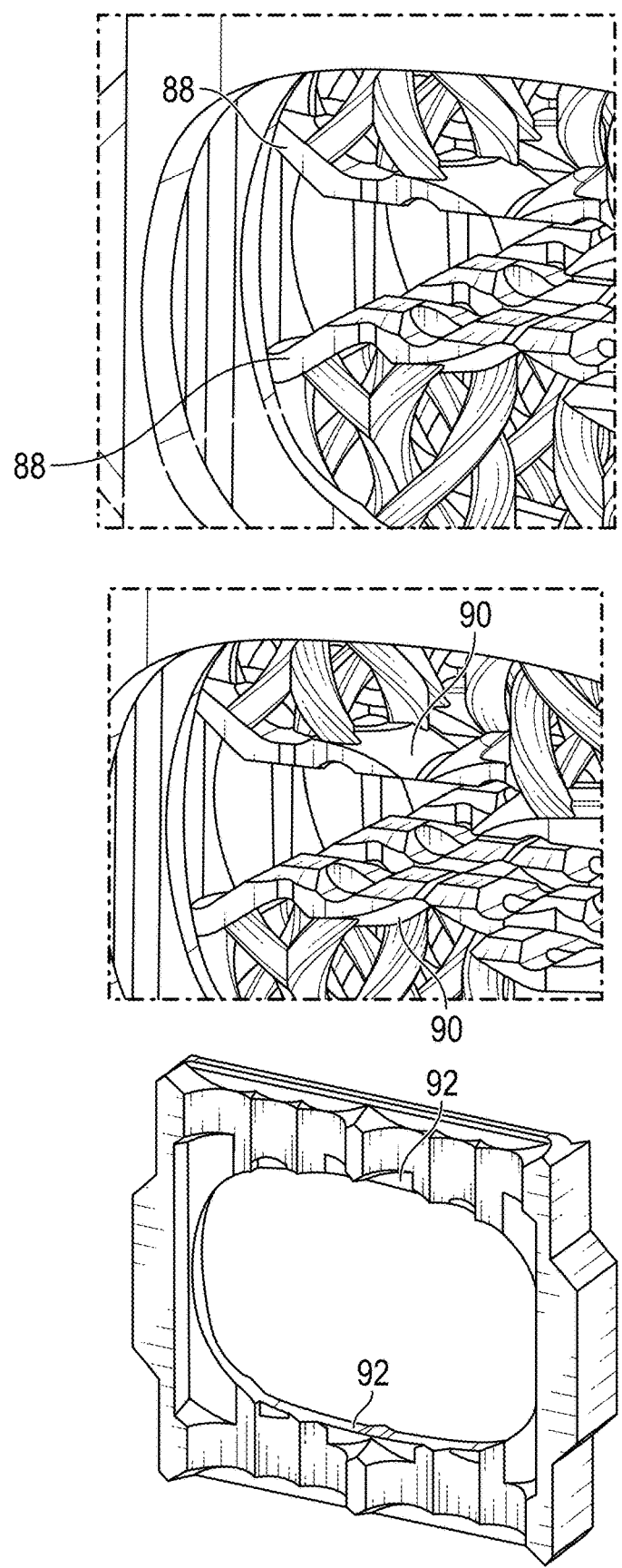
FIG. 38 shows views of portions of the expandable interbody spacer of FIG. 36.

FIGS. 36-38 show views of another illustrative embodiment of an expandable interbody spacer 66. In this embodiment, shape conformance, expansion, and distributed loading is provided by multiple independent coil sets forming segments 68 of top and bottom endplate surfaces that are effectively substantially contiguous and formed as a plurality of discrete and separate surface-forming elements, as illustrated by the top surface in the view of FIG. 36a and as illustrated on both top and bottom surfaces of the view of FIG. 36b. In some embodiments, the top and bottom endplate surfaces have a surface porosity adapted to promote bone on-growth and through-growth onto and through the spacer. In some embodiments, the structure of the spacer 66 extending between the first endplate surface and the second endplate surface includes a stiffness substantially equivalent to a typical stiffness of cortical bone of vertebral bodies adjacent to a space into which the spacer 66 is designed for insertion. Such loads are transmitted from the top endplate surface through the upper coil sets then through the lower coil sets to the lower endplate surface. This is facilitated in part by longitudinal members 70 (see FIG. 8) of the frame that transmit a clamping load between adjacent coil sets as a clamping force is applied at one end of the spacer 66. As the clamping force is applied, the interleaved coil sets and the longitudinal members 70 engage with each other such that forces applied to upper coil sets are transmitted through the longitudinal members 70 to lower coil sets, such that vertical forces are not applied to the stiffer external frame 71. Accordingly, the longitudinal members 70 of some embodiments have a stiffness that does not exceed twice the stiffness of the typical cortical bone of the vertebral bodies. Longitudinal members 70 inserted into the frame transmit a clamping load between ends of arch coil stacks to provide a shape-locking mechanism. Local load transmission is provided by multiple arch pieces that are contained and guided by the frame but do not transmit vertical load into the frame. The coils are actuated by a balloon or bellows 72 (one example of the balloon or bellows 72 is illustrated in FIG. 17 as bladder 28, while balloon or bellows 72 is illustrated in dotted format in FIG. 36, as being inside the expandable interbody spacer 66 it is not visible in the perspective view) inserted between upper coil sets and lower coil sets that acts as an expansion mechanism for uniform force distribution to selectively apply a distracting force between the top endplate surface and the bottom endplate surface. Then the shape is locked by compression of the arch coil stack using, for example, a screw compressor 75 inserted at threaded receptacle 74, one end of the spacer 66. This step of locking the shape occurs by a mechanism that acts separately or independently from the distraction mechanism provided by the balloon or bellows 72.

As illustrated at 76 in the view of FIG. 36b, coils are joined in groups of 2 or 3 coils. This prevents coil rotation to improve ability to compress the entire coil stack and not leave dead spots. This improves spatial efficiency and coil mutual support. As illustrated at 78 in the view of FIG. 36b, a spacer piece (shown as removed for fabrication) is moved to a proximal end of the implant to improve spatial balance of active and auxiliary space and proximal and distal ends. Increased stiffness at the proximal end also improves the ability of the locking element to transmit load evenly into first layers of arch-coil stack and obtain full shape locking.

As illustrated at 80 in the upper view of FIG. 37, corner coil sets are formed as groups of 3 coils instead of 2 to allow smoother transition at the frame juncture 82, increasing strength and allowing for a slower transition. As illustrated at 84, the nose is extended and the taper increased to facilitate insertion. As illustrated at 86 in the lower view of FIG. 37, support points are moved from the center of coil to the juncture between adjacent coils to reduce the number of points needing support during fabrication.

As illustrated at 88 in the upper view of FIG. 38, coils near wall of arches angle towards the adjacent coil juncture to eliminate the need for a separate support point during fabrication. Support stringers near the arch wall had proved very difficult to remove in previous designs. As illustrated at 90 in the lower left view of FIG. 38, stops are enlarged to prevent coils from being ejected during support removal or balloon/bellows inflation. As illustrated at 92 in the lower right view of FIG. 38, the arch roof is changed from flat to slightly curved to reduce probability of cracking during fabrication.

The balloon or bellows either occupies the rectangular envelope defined by the coils reaching a fully expanded state, or as an equivalent circular envelope having sufficient perimeter at any axial location to fill the rectangular envelope. This would allow fabrication by welding layers to create a rectangular-shape bellows, or by creation of a monolithic circular-section balloon.

Embodiments of the invention accordingly provide significant advantages over existing expanding interbody spacers. The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. An expandable interbody spacer comprising:
    a first endplate surface located on a first side of the spacer and adapted to contact a vertebral endplate surface of a first vertebral body;
    a second endplate surface located on a second, opposed, side of the spacer and adapted to contact a vertebral endplate surface of a second, opposed, vertebral body;
    an expansion mechanism adapted to selectively apply a distracting force between the first endplate surface and the second endplate surface, whereby actuation of the expansion mechanism causes the spacer to transition between a compressed insertion configuration to an expanded fusion configuration; and
    a shape-locking mechanism adapted to lock the first endplate surface and the second endplate surface in the expanded fusion configuration, wherein the shape-locking mechanism operates independently of actuation of the expansion mechanism, and wherein the shape-locking mechanism functions by application of a clamping force substantially perpendicular to a direction extending between the first endplate surface and the second endplate surface;
    wherein the first endplate surface and the second endplate surface are conformable to the first vertebral endplate surface and the second vertebral endplate surface.

2. The expandable interbody spacer as recited in claim 1, wherein the first endplate surface is substantially contiguous and the second endplate surface is substantially contiguous.

3. The expandable interbody spacer as recited in claim 2, wherein the first endplate surface and the second endplate surface comprise a deformable material.

4. The expandable interbody spacer as recited in claim 1, wherein the first endplate surface and the second endplate surface are each formed from a plurality of discrete and separate surface-forming elements.

5. The expandable interbody spacer as recited in claim 1, wherein the first endplate surface and the second endplate surface comprise a surface having a porosity adapted to promote bone on-growth and through-growth onto and through the spacer.

6. The expandable interbody spacer as recited in claim 1, wherein a structure of the spacer extending between the first endplate surface and the second endplate surface comprises a stiffness substantially equivalent to a stiffness of cortical bone of the first and second vertebral bodies.

7. The expandable interbody spacer as recited in claim 6, wherein loads applied to the first endplate surface are transmitted to the second endplate surface substantially without being distributed to a portion of the spacer having a stiffness greater than twice the stiffness of cortical bone of the first and second vertebral bodies.

8. An expandable interbody spacer comprising:
    a first endplate surface located on a first side of the spacer and adapted to contact a vertebral endplate surface of a first vertebral body;
    a second endplate surface located on a second, opposed, side of the spacer and adapted to contact a vertebral endplate surface of a second, opposed, vertebral body;
    an expansion mechanism adapted to selectively apply a distracting force between the first endplate surface and the second endplate surface, whereby actuation of the expansion mechanism causes the spacer to transition between a compressed insertion configuration to an expanded fusion configuration; and
    a shape-locking mechanism adapted to lock the first endplate surface and the second endplate surface in the expanded fusion configuration, wherein the shape-locking mechanism operates independently of actuation of the expansion mechanism, and wherein the shape-locking mechanism functions by application of a clamping force substantially perpendicular to a direction extending between the first endplate surface and the second endplate surface;
    wherein a structure of the spacer extending between the first endplate surface and the second endplate surface comprises a stiffness substantially equivalent to a stiffness of cortical bone of the first and second vertebral bodies.

9. The expandable interbody spacer as recited in claim 8, wherein the first endplate surface and the second endplate surface are conformable to the first vertebral endplate surface and the second vertebral endplate surface.

10. The expandable interbody spacer as recited in claim 9, wherein the first endplate surface and the second endplate surface are each formed from a plurality of discrete and separate surface-forming elements.

11. The expandable interbody spacer as recited in claim 8, wherein the first endplate surface and the second endplate surface comprise a surface having a porosity adapted to promote bone on-growth and through-growth onto and through the spacer.

12. The expandable interbody spacer as recited in claim 11, wherein a structure of the spacer extending between the first endplate surface and the second endplate surface comprises a porosity adapted to promote bone through-growth through the spacer.

13. The expandable interbody spacer as recited in claim 8, wherein loads applied to the first endplate surface are transmitted to the second endplate surface substantially without being distributed to a portion of the spacer having a stiffness greater than twice the stiffness of cortical bone of the first and second vertebral bodies.

14. An expandable interbody spacer comprising:
 a first endplate surface located on a first side of the spacer and adapted to contact a vertebral endplate surface of a first vertebral body;
 a second endplate surface located on a second, opposed, side of the spacer and adapted to contact a vertebral endplate surface of a second, opposed, vertebral body;
 an expansion mechanism adapted to selectively apply a distracting force between the first endplate surface and the second endplate surface, whereby actuation of the expansion mechanism causes the spacer to transition between a compressed insertion configuration to an expanded fusion configuration; and
 a shape-locking mechanism adapted to lock the first endplate surface and the second endplate surface in the expanded fusion configuration, wherein the shape-locking mechanism operates independently of actuation of the expansion mechanism, and wherein the shape-locking mechanism functions by application of a clamping force substantially perpendicular to a direction extending between the first endplate surface and the second endplate surface;
 wherein the first endplate surface and the second endplate surface and a structure extending between the first endplate surface and the second endplate surface all comprise a porosity adapted to promote bone on-growth and through-growth through the spacer.

15. The expandable interbody spacer as recited in claim 14, wherein the porosity consists essentially of pores no larger than 650 microns.

16. The expandable interbody spacer as recited in claim 15, wherein the porosity consists essentially of pores no larger than 500 microns.

17. The expandable interbody spacer as recited in claim 14, wherein the first endplate surface and the second endplate surface are conformable to the first vertebral endplate surface and the second vertebral endplate surface.

18. The expandable interbody spacer as recited in claim 17, wherein the first endplate surface and the second endplate surface are each formed from a plurality of discrete and separate surface-forming elements.

19. An expandable interbody spacer comprising:
 a first endplate surface located on a first side of the spacer and adapted to contact a vertebral endplate surface of a first vertebral body;
 a second endplate surface located on a second, opposed, side of the spacer and adapted to contact a vertebral endplate surface of a second, opposed, vertebral body;
 an expansion mechanism adapted to selectively apply a distracting force between the first endplate surface and the second endplate surface, whereby actuation of the expansion mechanism causes the spacer to transition between a compressed insertion configuration to an expanded fusion configuration; and
 a shape-locking mechanism adapted to lock the first endplate surface and the second endplate surface in the expanded fusion configuration, wherein the shape-locking mechanism operates independently of actuation of the expansion mechanism, and wherein the shape-locking mechanism functions by application of a clamping force substantially perpendicular to a direction extending between the first endplate surface and the second endplate surface;
 wherein loads applied to the first endplate surface are transmitted to the second endplate surface substantially without being distributed to a portion of the spacer having a stiffness greater than twice the stiffness of cortical bone of the first and second vertebral bodies, thereby minimizing a risk of post-implant subsidence.

* * * * *